United States Patent [19]

Kumonaka et al.

[11] Patent Number: 5,635,505
[45] Date of Patent: Jun. 3, 1997

[54] 1,4-BENZOXAZINE-2-ACETIC ACID COMPOUND, METHOD FOR PRODUCTION THEREOF AND USE THEREOF

[75] Inventors: Takahiro Kumonaka, Hadano; Takema Hase; Tomoji Aotsuka, both of Hamura; Toshio Kurihara; Yoshiyuki Nakamura, both of Shizuoka; Tetsuo Matsui, Tsukuba; Hiromichi Ishikawa, Kobe; Fujio Kobayashi, Shizuoka, all of Japan

[73] Assignees: Senju Pharmaceutical Co., Ltd.; The Green Cross Corporation, both of Osaka, Japan

[21] Appl. No.: 666,326
[22] PCT Filed: Jan. 6, 1994
[86] PCT No.: PCT/JP94/00005
§ 371 Date: Jul. 3, 1996
§ 102(e) Date: Jul. 3, 1996
[87] PCT Pub. No.: WO95/18805
PCT Pub. Date: Jul. 13, 1995
[51] Int. Cl.$^6$ .................. A61K 31/535; C07D 417/06
[52] U.S. Cl. ........................... 514/230.5; 544/105
[58] Field of Search .................... 544/105; 514/230.5

[56] References Cited

U.S. PATENT DOCUMENTS 4,824,833  4/1989  Iijima et al. ............................ 514/230.5
4,962,200  10/1990  Kihara et al. ............................ 544/333

*Primary Examiner*—Philip I. Datlow
*Assistant Examiner*—Sabiha N. Qazi
*Attorney, Agent, or Firm*—Sughrue, Mion, Zinn, Macpeak & Seas

[57] ABSTRACT

A 1,4-benzoxazine-2-acetic acid compound of the formula (I)

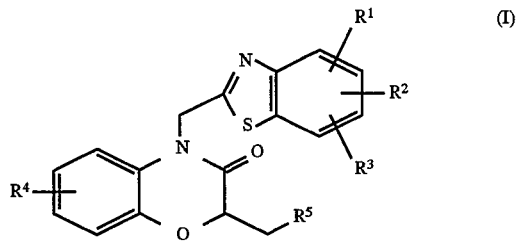

wherein each symbol is as defined in the specification, a pharmaceutically acceptable salt thereof, a method for production thereof, and a pharmaceutical composition, an aldose reductase inhibitor and an agent for the prevention and/or treatment of the complications of diabetes, which contain the same. The compound (I) of the present invention and pharmaceutically acceptable salts thereof have aldose reductase inhibitory action and are superior in safety. Accordingly, they are useful as an agent for the prevention and/or treatment of the complications of diabetes such as faulty union of corneal injury, cataract, neurosis, retinopathy and nephropathy, in particular, cataract and neurosis.

11 Claims, No Drawings

1,4-BENZOXAZINE-2-ACETIC ACID COMPOUND, METHOD FOR PRODUCTION THEREOF AND USE THEREOF

This is a 35USC371 National Stage of International Application PCT/JP94/00005, filed Jan. 6, 1994.

TECHNICAL FIELD

The present invention relates to novel 1,4-benzoxazine-2-acetic acid compounds having superior aldose reductase inhibitory activity, pharmaceutically acceptable salts thereof, methods for production thereof, and pharmaceutical use thereof. The compounds of the present invention and pharmaceutically acceptable salts thereof are useful as agents for the prevention and treatment of the complications of diabetes, such as diabetic cataract, retinopathy, nephropathy and neurosis.

BACKGROUND ART

Traditionally, blood sugar regulators such as insulin and synthetic hypoglycemic agents have been widely used for treating diabetes. Diabetes is a disease which accompanies various complications which are hardly prevented from developing by a mere control of blood sugar, and a new therapeutic agent for the complications of diabetes has been demanded.

Accumulation of and increase in sorbitol and galactitol in tissues, which are caused by chronic hyperglycemia, have been recently drawing attention as the mechanism of the onset of the complications of diabetes.

Some literatures suggest that a compound having an inhibitory action on the activity of aldose reductase, which is an enzyme capable of converting aldose such as glucose or galactose into sorbitol or galactitol, is useful for the treatment of the complications of diabetes, such as cataract, neurosis, nephropathy and retinopathy [J. H. Kinoshita et al. Biochem. Biophys. Acta, 158, 472 (968), Richard Poulson et al, Biochem. Pharmacol., 32, 1495 (1983) and D. Dvornik et al, Science, 182, 1145 (1973)].

Based on the foregoing, the study is directed to the prevention and treatment of the complications of diabetes by the inhibition of aldose reductase activity to ultimately inhibit accumulation of polyols such as sorbitol and galactitol.

Of the compounds synthesized for this end, Japanese Patent Unexamined Publication Nos. 40264/1986 and 107970/1988 describe that various 1,4-benzothiazine-4-acetic acid compounds have aldose reductase inhibitory action. Yet, the development of an agent for the prophylaxis and treatment of the complications of diabetes, which has a still more excellent aldose reductase inhibitory action, is desired.

DISCLOSURE OF THE INVENTION

In view of the above, the present inventors have conducted intensive studies with the aim of developing a therapeutic agent for the complications of diabetes, which has an aldose reductase inhibitory action, and found that certain benzoxazine compounds can accomplish such object and completed the present invention.

Accordingly, the present invention relates to a 1,4-benzoxazine-2-acetic acid compound of the following formula (I)

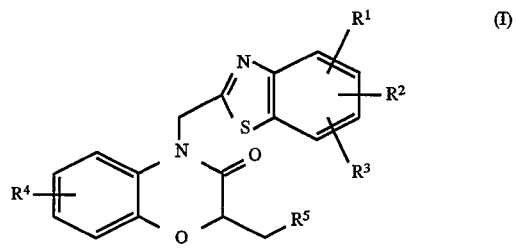

wherein $R^1$, $R^2$ and $R^3$ may be the same or different and each is a hydrogen atom, a lower alkyl, an alkoxy, a halogen atom or a hydroxy, $R^4$ is a hydrogen atom, a halogen atom, a lower alkyl or an alkoxy and $R^5$ is an optionally esterified carboxyl, and pharmaceutically acceptable salts thereof.

The present invention also relates to methods for producing 1,4-benzoxazine-2-acetic acid compounds of the above formula (I) and pharmaceutically acceptable salts thereof, comprising (a) reacting a compound of the formula (II)

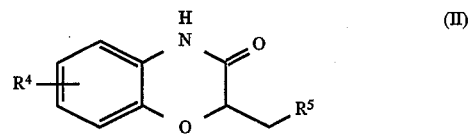

wherein $R^4$ and $R^5$ are as defined above, or a salt thereof, with a compound of the formula (III)

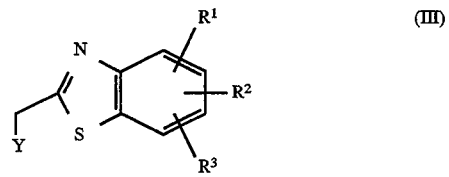

wherein $R^1$, $R^2$ and $R^3$ are as defined above, and Y is a halogen atom or $—OSO_2R^6$ wherein $R^6$ is lower alkyl, trifluoromethyl or optionally substituted phenyl, or (b) reacting a compound of the formula (IV)

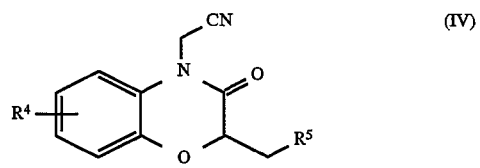

wherein $R^4$ and $R^5$ are as defined above, or a salt thereof, with a compound of the formula (V)

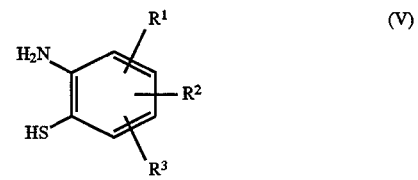

wherein $R^1$, $R^2$ and $R^3$ are as defined above, or an acid addition salt thereof, followed by, on demand, hydrolysis of the compound obtained in the above (a) or (b).

The present invention also provides a pharmaceutical composition containing the above-mentioned 1,4-benzoxazine-2-acetic acid compound or a pharmaceutically acceptable salt thereof; in particular, an aldose reductase inhibitor and an agent for the prevention and treatment of the complications of diabetes.

The compound of the present invention which is represented by the above formula (I) [hereinafter sometimes referred to as compound (I) of the present invention] is a compound having a novel structure essentially having, as a basic structure, 1,4-benzoxazine-2-acetic acid moiety.

The respective symbols used in the present specification are explained in the following.

The halogen atom at $R^1$–$R^4$ and Y includes, for example, fluorine atom, chlorine atom, bromine atom and iodine atom. The lower alkyl at $R^1$–$R^4$ and $R^6$ is preferably a straight or branched alkyl having 1 to 6 carbon atoms, such as methyl, ethyl, propyl, isopropyl, butyl, isobutyl, sec-butyl, tert-butyl, pentyl, isopentyl, sec-pentyl, tert-pentyl, hexyl, isohexyl, sec-hexyl and tert-hexyl. Such lower alkyl may be substituted by aryl, amino, halogen atom (those mentioned above), etc.

The alkoxy at $R^1$–$R^4$ is preferably a straight or branched alkoxy having 1 to 6 carbon atoms, such as methoxy, ethoxy, propoxy, isopropoxy, butoxy, isobutoxy, sec-butoxy, tert-butoxy, pentyloxy, isopentyloxy, sec-pentyloxy, tert-pentyloxy, hexyloxy, isohexyloxy, sec-hexyloxy and tert-hexyloxy. These alkoxy may be substituted by aryl, amino, halogen atom (those mentioned above), etc.

The esterified carboxyl at $R^5$ includes, for example, lower alkoxycarbonyl such as methoxycarbonyl, ethoxycarbonyl, propoxycarbonyl, isopropoxycarbonyl, butoxycarbonyl, isobutoxycarbonyl and tert-butoxycarbonyl, and aryloxycarbonyl which may have substituent(s) on the benzene ring and benzyloxycarbonyl. The substituents for the aryloxycarbonyl which may have substituent(s) on the benzene ring include, for example, halogen atom (those mentioned above), alkyl, alkoxy and nitro.

The substituents for the optionally substituted phenyl at $R^6$ include, for example, lower alkyl (those mentioned above), halogen atom (those mentioned above) and nitro.

$R^1$, $R^2$ and $R^3$ of the formula (I) can be bonded at an optional position from 4 to 7 positions of benzothiazole, with preference given to 4, 5 and 7-positions. It is also preferable that at least one of $R^1$, $R^2$ and $R^3$ be fluorine atom. It is particularly preferable that the halogen atom be fluorine atom.

$R^4$ of the formula (I) can take any optional position from 5 to 8 positions of benzoxazine ring, with preference given to 6 and 7-positions. $R^4$ is preferably hydrogen atom, lower alkyl or halogen atom, and most preferably hydrogen atom, methyl, chlorine atom or fluorine atom.

$R^5$ of the formula (I) is preferably carboxyl.

The compound (I) of the present invention has an asymmetric carbon and can exist as stereoisomers, which are also encompassed in the present invention. They can be resolved into pure isomers on demand by a conventional method.

The pharmaceutically acceptable salts of the compound (I) of the present invention include, for example, salts with inorganic base (e.g., alkali metals such as lithium, sodium and potassium; alkaline earth metals such as calcium, magnesium and beryllium; and aluminum) or with organic base (e.g., triethylamine and pyridine).

Typical compounds (I) of the present invention are, for example, the following compounds.

2-[4-(benzothiazol-2-yl)methyl-3,4-dihydro-3-oxo-2H-1,4-benzoxazin-2-yl]acetic acid
2-[4-(4-bromobenzothiazol-2-yl)methyl-3,4-dihydro-3-oxo-2H-1,4-benzoxazin-2-yl]acetic acid
2-[4-(5-bromobenzothiazol-2-yl)methyl-3,4-dihydro-3-oxo-2H-1,4-benzoxazin-2-yl]acetic acid
2-[4-(6-bromobenzothiazol-2-yl)methyl-3,4-dihydro-3-oxo-2H-1,4-benzoxazin-2-yl]acetic acid
2-[4-(7-bromobenzothiazol-2-yl)methyl-3,4-dihydro-3-oxo-2H-1,4-benzoxazin-2-yl]acetic acid
2-[4-(4-chlorobenzothiazol-2-yl)methyl-3,4-dihydro-3-oxo-2H-1,4-benzoxazin-2-yl]acetic acid
2-[4-(5-chlorobenzothiazol-2-yl)methyl-3,4-dihydro-3-oxo-2H-1,4-benzoxazin-2-yl]acetic acid
2-[4-(6-chlorobenzothiazol-2-yl)methyl-3,4-dihydro-3-oxo-2H-1,4-benzoxazin-2-yl]acetic acid
2-[4-(7-chlorobenzothiazol-2-yl)methyl-3,4-dihydro-3-oxo-2H-1,4-benzoxazin-2-yl]acetic acid
ethyl 2-[4-(4-fluorobenzothiazol-2-yl)methyl-3,4-dihydro-3-oxo-2H-1,4-benzoxazin-2-yl]acetate
2-[4-(4-fluorobenzothiazol-2-yl)methyl-3,4-dihydro-3-oxo-2H-1,4-benzoxazin-2-yl]acetic acid
ethyl 2-[4-(5-fluorobenzothiazol-2-yl)methyl-3,4-dihydro-3-oxo-2H-1,4-benzoxazin-2-yl]acetate
2-[4-(5-fluorobenzothiazol-2-yl)methyl-3,4-dihydro-3-oxo-2H-1,4-benzoxazin-2-yl]acetic acid
ethyl 2-[4-(6-fluorobenzothiazol-2-yl)methyl-3,4-dihydro-3-oxo-2H-1,4-benzoxazin-2-yl]acetate
2-[4-(6-fluorobenzothiazol-2-yl)methyl-3,4-dihydro-3-oxo-2H-1,4-benzoxazin-2-yl]acetic acid
ethyl 2-[4-(7-fluorobenzothiazol-2-yl)methyl-3,4-dihydro-3-oxo-2H-1,4-benzoxazin-2-yl]acetate
2-[4-(7-fluorobenzothiazol-2-yl)methyl-3,4-dihydro-3-oxo-2H-1,4-benzoxazin-2-yl]acetic acid
2-[4-(4,5-dichlorobenzothiazol-2-yl)methyl-3,4-dihydro-3-oxo-2H-1,4-benzoxazin-2-yl]acetic acid
2-[4-(4,6-dichlorobenzothiazol-2-yl)methyl-3,4-dihydro-3-oxo-2H-1,4-benzoxazin-2-yl]acetic acid
2-[4-(4,7-dichlorobenzothiazol-2-yl)methyl-3,4-dihydro-3-oxo-2H-1,4-benzoxazin-2-yl]acetic acid
2-[4-(5,6-dichlorobenzothiazol-2-yl)methyl-3,4-dihydro-3-oxo-2H-1,4-benzoxazin-2-yl]acetic acid
2-[4-(5,7-dichlorobenzothiazol-2-yl)methyl-3,4-dihydro-3-oxo-2H-1,4-benzoxazin-2-yl]acetic acid
2-[4-(6,7-dichlorobenzothiazol-2-yl)methyl-3,4-dihydro-3-oxo-2H-1,4-benzoxazin-2-yl]acetic acid
2-[4-(4,5,6-trichlorobenzothiazol-2-yl)methyl-3,4-dihydro-3-oxo-2H-1,4-benzoxazin-2-yl]acetic acid
2-[4-(4,5,7-trichlorobenzothiazol-2-yl)methyl-3,4-dihydro-3-oxo-2H-1,4-benzoxazin-2-yl]acetic acid
2-[4-(4,6,7-trichlorobenzothiazol-2-yl)methyl-3,4-dihydro-3-oxo-2H-1,4-benzoxazin-2-yl]acetic acid
2-[4-(5,6,7-trichlorobenzothiazol-2-yl)methyl-3,4-dihydro-3-oxo-2H-1,4-benzoxazin-2-yl]acetic acid
ethyl 2-[4-(4,5-difluorobenzothiazol-2-yl)methyl-3,4-dihydro-3-oxo-2H-1,4-benzoxazin-2-yl]acetate
2-[4-(4,5-difluorobenzothiazol-2-yl)methyl-3,4-dihydro-3-oxo-2H-1,4-benzoxazin-2-yl]acetic acid
ethyl 2-[4-(4,6-difluorobenzothiazol-2-yl)methyl-3,4-dihydro-3-oxo-2H-1,4-benzoxazin-2-yl]acetate
2-[4-(4,6-difluorobenzothiazol-2-yl)methyl-3,4-dihydro-3-oxo-2H-1,4-benzoxazin-2-yl]acetic acid
ethyl 2-[4-(4,7-difluorobenzothiazol-2-yl)methyl-3,4-dihydro-3-oxo-2H-1,4-benzoxazin-2-yl]acetate
2-[4-(4,7-difluorobenzothiazol-2-yl)methyl-3,4-dihydro-3-oxo-2H-1,4-benzoxazin-2-yl]acetic acid
ethyl 2-[4-(5,6-difluorobenzothiazol-2-yl)methyl-3,4-dihydro-3-oxo-2H-1,4-benzoxazin-2-yl]acetate
2-[4-(5,6-difluorobenzothiazol-2-yl)methyl-3,4-dihydro-3-oxo-2H-1,4-benzoxazin-2-yl]acetic acid
ethyl 2-[4-(5,7-difluorobenzothiazol-2-yl)methyl-3,4-dihydro-3-oxo-2H-1,4-benzoxazin-2-yl]acetate
2-[4-(5,7-difluorobenzothiazol-2-yl)methyl-3,4-dihydro-3-oxo-2H-1,4-benzoxazin-2-yl]acetic acid
ethyl 2-[4-(6,7-difluorobenzothiazol-2-yl)methyl-3,4-dihydro-3-oxo-2H-1,4-benzoxazin-2-yl]acetate
2-[4-(6,7-difluorobenzothiazol-2-yl)methyl-3,4-dihydro-3-oxo-2H-1,4-benzoxazin-2-yl]acetic acid ethyl 2-[4-(4,5,6-trifluorobenzothiazol-2-yl)methyl-3,4-dihydro-3-oxo-2H-1,4-benzoxazin-2-yl]acetate
2-[4-(4,5,6-trifluorobenzothiazol-2-yl)methyl-3,4-dihydro-3-oxo-2H-1,4-benzoxazin-2-yl]acetic acid
ethyl 2-[4-(4,5,7-trifluorobenzothiazol-2-yl)methyl-3,4-dihydro-3-oxo-2H-1,4-benzoxazin-2-yl]acetate
2-[4-(4,5,7-trifluorobenzothiazol-2-yl)methyl-3,4-dihydro-3-oxo-2H-1,4-benzoxazin-2-yl]acetic acid
ethyl 2-[4-(4,6,7-trifluorobenzothiazol-2-yl)methyl-3,4-dihydro-3-oxo-2H-1,4-benzoxazin-2-yl]acetate
2-[4-(4,6,7-trifluorobenzothiazol-2-yl)methyl-3,4-dihydro-3-oxo-2H-1,4-benzoxazin-2-yl]acetic acid
ethyl 2-[4-(5,6,7-trifluorobenzothiazol-2-yl)methyl-3,4-dihydro-3-oxo-2H-1,4-benzoxazin-2-yl]acetate
2-[4-(5,6,7-trifluorobenzothiazol-2-yl)methyl-3,4-dihydro-3-oxo-2H-1,4-benzoxazin-2-yl]acetic acid
2-[4-(4-chloro-5-fluorobenzothiazol-2-yl)methyl-3,4-dihydro-3-oxo-2H-1,4-benzoxazin-2-yl]acetic acid
2-[4-(4-chloro-7-fluorobenzothiazol-2-yl)methyl-3,4-dihydro-3-oxo-2H-1,4-benzoxazin-2-yl]acetic acid
2-[4-(5-chloro-4-fluorobenzothiazol-2-yl)methyl-3,4-dihydro-3-oxo-2H-1,4-benzoxazin-2-yl]acetic acid
2-[4-(5-chloro-7-fluorobenzothiazol-2-yl)methyl-3,4-dihydro-3-oxo-2H-1,4-benzoxazin-2-yl]acetic acid
2-[4-(6-chloro-7-fluorobenzothiazol-2-yl)methyl-3,4-dihydro-3-oxo-2H-1,4-benzoxazin-2-yl]acetic acid
2-[4-(7-chloro-4-fluorobenzothiazol-2-yl)methyl-3,4-dihydro-3-oxo-2H-1,4-benzoxazin-2-yl]acetic acid
2-[4-(7-chloro-5-fluorobenzothiazol-2-yl)methyl-3,4-dihydro-3-oxo-2H-1,4-benzoxazin-2-yl]acetic acid
2-[4-(7-chloro-6-fluorobenzothiazol-2-yl)methyl-3,4-dihydro-3-oxo-2H-1,4-benzoxazin-2-yl]acetic acid
2-[4-(4,5-dichloro-6-fluorobenzothiazol-2-yl)methyl-3,4-dihydro-3-oxo-2H-1,4-benzoxazin-2-yl]acetic acid
2-[4-(4,6-dichloro-5-fluorobenzothiazol-2-yl)methyl-3,4-dihydro-3-oxo-2H-1,4-benzoxazin-2-yl]acetic acid
2-[4-(4-chloro-5,6-difluorobenzothiazol-2-yl)methyl-3,4-dihydro-3-oxo-2H-1,4-benzoxazin-2-yl]acetic acid
2-[4-(5,6-dichloro-4-fluorobenzothiazol-2-yl)methyl-3,4-dihydro-3-oxo-2H-1,4-benzoxazin-2-yl]acetic acid
2-[4-(6-chloro-4,5-difluorobenzothiazol-2-yl)methyl-3,4-dihydro-3-oxo-2H-1,4-benzoxazin-2-yl]acetic acid
2-[4-(5-chloro-4,6-difluorobenzothiazol-2-yl)methyl-3,4-dihydro-3-oxo-2H-1,4-benzoxazin-2-yl]acetic acid
2-[4-(4,5-dichloro-7-fluorobenzothiazol-2-yl)methyl-3,4-dihydro-3-oxo-2H-1,4-benzoxazin-2-yl]acetic acid
2-[4-(4,7-dichloro-5-fluorobenzothiazol-2-yl)methyl-3,4-dihydro-3-oxo-2H-1,4-benzoxazin-2-yl]acetic acid
2-[4-(4-chloro-5,7-difluorobenzothiazol-2-yl)methyl-3,4-dihydro-3-oxo-2H-1,4-benzoxazin-2-yl]acetic acid
2-[4-(5,7-dichloro-4-fluorobenzothiazol-2-yl)methyl-3,4-dihydro-3-oxo-2H-1,4-benzoxazin-2-yl]acetic acid
2-[4-(7-chloro-4,5-difluorobenzothiazol-2-yl)methyl-3,4-dihydro-3-oxo-2H-1,4-benzoxazin-2-yl]acetic acid
2-[4-(5-chloro-4,7-difluorobenzothiazol-2-yl)methyl-3,4-dihydro-3-oxo-2H-1,4-benzoxazin-2-yl]acetic acid
2-[4-(4,6-dichloro-7-fluorobenzothiazol-2-yl)methyl-3,4-dihydro-3-oxo-2H-1,4-benzoxazin-2-yl]acetic acid
2-[4-(4,7-dichloro-6-fluorobenzothiazol-2-yl)methyl-3,4-dihydro-3-oxo-2H-1,4-benzoxazin-2-yl]acetic acid
2-[4-(4-chloro-6,7-difluorobenzothiazol-2-yl)methyl-3,4-dihydro-3-oxo-2H-1,4-benzoxazin-2-yl]acetic acid
2-[4-(6,7-dichloro-4-fluorobenzothiazol-2-yl)methyl-3,4-dihydro-3-oxo-2H-1,4-benzoxazin-2-yl]acetic acid
2-[4-(7-chloro-4,6-difluorobenzothiazol-2-yl)methyl-3,4-dihydro-3-oxo-2H-1,4-benzoxazin-2-yl]acetic acid
2-[4-(6-chloro-4,7-difluorobenzothiazol-2-yl)methyl-3,4-dihydro-3-oxo-2H-1,4-benzoxazin-2-yl]acetic acid
2-[4-(5,7-dichloro-6-fluorobenzothiazol-2-yl)methyl-3,4-dihydro-3-oxo-2H-1,4-benzoxazin-2-yl]acetic acid
2-[4-(5-chloro-6,7-difluorobenzothiazol-2-yl)methyl-3,4-dihydro-3-oxo-2H-1,4-benzoxazin-2-yl]acetic acid
2-[4-(6,7-dichloro-5-fluorobenzothiazol-2-yl)methyl-3,4-dihydro-3-oxo-2H-1,4-benzoxazin-2-yl]acetic acid
2-[4-(7-chloro-5,6-difluorobenzothiazol-2-yl)methyl-3,4-dihydro-3-oxo-2H-1,4-benzoxazin-2-yl]acetic acid
2-[4-(6-chloro-5,7-difluorobenzothiazol-2-yl)methyl-3,4-dihydro-3-oxo-2H-1,4-benzoxazin-2-yl]acetic acid
2-[4-(4-fluorobenzothiazol-2-yl)methyl-5-methyl-3,4-dihydro-3-oxo-2H-1,4-benzoxazin-2-yl]acetic acid
2-[5-ethyl-4-(5-fluorobenzothiazol-2-yl)methyl-3,4-dihydro-3-oxo-2H-1,4-benzoxazin-2-yl]acetic acid
2-[4-(5-fluorobenzothiazol-2-yl)methyl-5-propyl-3,4-dihydro-3-oxo-2H-1,4-benzoxazin-2-yl]acetic acid
2-[4-(5-fluorobenzothiazol-2-yl)methyl-5-isopropyl-3,4-dihydro-3-oxo-2H-1,4-benzoxazin-2-yl]acetic acid
2-[4-(6-fluorobenzothiazol-2-yl)methyl-5-methyl-3,4-dihydro-3-oxo-2H-1,4-benzoxazin-2-yl]acetic acid
2-[4-(7-fluorobenzothiazol-2-yl)methyl-5-methyl-3,4-dihydro-3-oxo-2H-1,4-benzoxazin-2-yl]acetic acid
2-[4-(4,5-dichlorobenzothiazol-2-yl)methyl-5-methyl-3,4-dihydro-3-oxo-2H-1,4-benzoxazin-2-yl]acetic acid
2-[4-(4,6-dichlorobenzothiazol-2-yl)methyl-5-methyl-3,4-dihydro-3-oxo-2H-1,4-benzoxazin-2-yl]acetic acid
2-[4-(4,7-dichlorobenzothiazol-2-yl)methyl-5-methyl-3,4-dihydro-3-oxo-2H-1,4-benzoxazin-2-yl]acetic acid
2-[4-(5,6-dichlorobenzothiazol-2-yl)methyl-5-methyl-3,4-dihydro-3-oxo-2H-1,4-benzoxazin-2-yl]acetic acid
2-[4-(5,7-dichlorobenzothiazol-2-yl)methyl-5-methyl-3,4-dihydro-3-oxo-2H-1,4-benzoxazin-2-yl]acetic acid
2-[4-(6,7-dichlorobenzothiazol-2-yl)methyl-5-methyl-3,4-dihydro-3-oxo-2H-1,4-benzoxazin-2-yl]acetic acid
2-[4-(4,5,6-trichlorobenzothiazol-2-yl)methyl-5-methyl-3,4-dihydro-3-oxo-2H-1,4-benzoxazin-2-yl]acetic acid
2-[4-(4,5,7-trichlorobenzothiazol-2-yl)methyl-5-methyl-3,4-dihydro-3-oxo-2H-1,4-benzoxazin-2-yl]acetic acid
2-[4-(4,6,7-trichlorobenzothiazol-2-yl)methyl-5-methyl-3,4-dihydro-3-oxo-2H-1,4-benzoxazin-2-yl]acetic acid
2-[4-(5,6,7-trichlorobenzothiazol-2-yl)methyl-5-methyl-3,4-dihydro-3-oxo-2H-1,4-benzoxazin-2-yl]acetic acid
methyl 2-[4-(4,5-difluorobenzothiazol-2-yl)methyl-5-methyl-3,4-dihydro-3-oxo-2H-1,4-benzoxazin-2-yl]acetate
2-[4-(4,5-difluorobenzothiazol-2-yl)methyl-5-methyl-3,4-dihydro-3-oxo-2H-1,4-benzoxazin-2-yl]acetic acid
methyl 2-[4-(4,6-difluorobenzothiazol-2-yl)methyl-5-methyl-3,4-dihydro-3-oxo-2H-1,4-benzoxazin-2-yl]acetate
2-[4-(4,6-difluorobenzothiazol-2-yl)methyl-5-methyl-3,4-dihydro-3-oxo-2H-1,4-benzoxazin-2-yl]acetic acid
methyl 2-[4-(4,7-difluorobenzothiazol-2-yl)methyl-5-methyl-3,4-dihydro-3-oxo-2H-1,4-benzoxazin-2-yl]acetate
2-[4-(4,7-difluorobenzothiazol-2-yl)methyl-5-methyl-3,4-dihydro-3-oxo-2H-1,4-benzoxazin-2-yl]acetic acid
methyl 2-[4-(5,6-difluorobenzothiazol-2-yl)methyl-5-methyl-3,4-dihydro-3-oxo-2H-1,4-benzoxazin-2-yl]acetate
2-[4-(5,6-difluorobenzothiazol-2-yl)methyl-5-methyl-3,4-dihydro-3-oxo-2H-1,4-benzoxazin-2-yl]acetic acid
methyl 2-[4-(5,7-difluorobenzothiazol-2-yl)methyl-5-methyl-3,4-dihydro-3-oxo-2H-1,4-benzoxazin-2-yl]acetate
2-[4-(5,7-difluorobenzothiazol-2-yl)methyl-5-methyl-3,4-dihydro-3-oxo-2H-1,4-benzoxazin-2-yl]acetic acid
methyl 2-[4-(6,7-difluorobenzothiazol-2-yl)methyl-5-methyl-3,4-dihydro-3-oxo-2H-1,4-benzoxazin-2-yl]acetate
2-[4-(6,7-difluorobenzothiazol-2-yl)methyl-5-methyl-3,4-dihydro-3-oxo-2H-1,4-benzoxazin-2-yl]acetic acid
methyl 2-[4-(4,5,6-trifluorobenzothiazol-2-yl)methyl-5-methyl-3,4-dihydro-3-oxo-2H-1,4-benzoxazin-2-yl]acetate 2-[4-(4,5,6-trifluorobenzothiazol-2-yl)methyl-5-methyl-3,4-dihydro-3-oxo-2H-1,4-benzoxazin-2-yl]acetic acid
methyl 2-[4-(4,5,7-trifluorobenzothiazol-2-yl)methyl-5-methyl-3,4-dihydro-3-oxo-2H-1,4-benzoxazin-2-yl]acetate
2-[4-(4,5,7-trifluorobenzothiazol-2-yl)methyl-5-methyl-3,4-dihydro-3-oxo-2H-1,4-benzoxazin-2-yl]acetic acid
methyl 2-[4-(4,6,7-trifluorobenzothiazol-2-yl)methyl-5-methyl-3,4-dihydro-3-oxo-2H-1,4-benzoxazin-2-yl]acetate
2-[4-(4,6,7-trifluorobenzothiazol-2-yl)methyl-5-methyl-3,4-dihydro-3-oxo-2H-1,4-benzoxazin-2-yl]acetic acid
methyl 2-[4-(5,6,7-trifluorobenzothiazol-2-yl)methyl-5-methyl-3,4-dihydro-3-oxo-2H-1,4-benzoxazin-2-yl]acetate
2-[4-(5,6,7-trifluorobenzothiazol-2-yl)methyl-5-methyl-3,4-dihydro-3-oxo-2H-1,4-benzoxazin-2-yl]acetic acid
2-[5-fluoro-4-(4-fluorobenzothiazol-2-yl)methyl-3,4-dihydro-3-oxo-2H-1,4-benzoxazin-2-yl]acetic acid
2-[5-fluoro-4-(5-fluorobenzothiazol-2-yl)methyl-3,4-dihydro-3-oxo-2H-1,4-benzoxazin-2-yl]acetic acid
2-[5-fluoro-4-(6-fluorobenzothiazol-2-yl)methyl-3,4-dihydro-3-oxo-2H-1,4-benzoxazin-2-yl]acetic acid
2-[5-fluoro-4-(7-fluorobenzothiazol-2-yl)methyl-3,4-dihydro-3-oxo-2H-1,4-benzoxazin-2-yl]acetic acid
2-[4-(4,5-dichlorobenzothiazol-2-yl)methyl-5-fluoro-3,4-dihydro-3-oxo-2H-1,4-benzoxazin-2-yl]acetic acid
2-[4-(4,6-dichlorobenzothiazol-2-yl)methyl-5-fluoro-5,4-dihydro-3-oxo-2H-1,4-benzoxazin-2-yl]acetic acid
2-[4-(4,7-dichlorobenzothiazol-2-yl)methyl-5-fluoro-3,4-dihydro-3-oxo-2H-1,4-benzoxazin-2-yl]acetic acid
2-[4-(5,6-dichlorobenzothiazol-2-yl)methyl-5-fluoro-3,4-dihydro-3-oxo-2H-1,4-benzoxazin-2-yl]acetic acid
2-[4-(5,7-dichlorobenzothiazol-2-yl)methyl-5-fluoro-3,4-dihydro-3-oxo-2H-1,4-benzoxazin-2-yl]acetic acid
2-[4-(6,7-dichlorobenzothiazol-2-yl)methyl-5-fluoro-3,4-dihydro-3-oxo-2H-1,4-benzoxazin-2-yl]acetic acid
2-[4-(4,5,6-trichlorobenzothiazol-2-yl)methyl-5-fluoro-3,4-dihydro-3-oxo-2H-1,4-benzoxazin-2-yl]acetic acid
2-[4-(4,5,7-trichlorobenzothiazol-2-yl)methyl-5-fluoro-3,4-dihydro-3-oxo-2H-1,4-benzoxazin-2-yl]acetic acid
2-[4-(4,6,7-trichlorobenzothiazol-2-yl)methyl-5-fluoro-3,4-dihydro-3-oxo-2H-1,4-benzoxazin-2-yl]acetic acid
2-[4-(5,6,7-trichlorobenzothiazol-2-yl)methyl-5-fluoro-3,4-dihydro-3-oxo-2H-1,4-benzoxazin-2-yl]acetic acid
ethyl 2-[5-fluoro-4-(4,5-difluorobenzothiazol-2-yl)methyl-3,4-dihydro-3-oxo-2H-1,4-benzoxazin-2-yl]acetate
2-[5-fluoro-4-(4,5-difluorobenzothiazol-2-yl)methyl-3,4-dihydro-3-oxo-2H-1,4-benzoxazin-2-yl]acetic acid
ethyl 2-[5-fluoro-4-(4,6-difluorobenzothiazol-2-yl)methyl-3,4-dihydro-3-oxo-2H-1,4-benzoxazin-2-yl]acetate
2-[5-fluoro-4-(4,6-difluorobenzothiazol-2-yl)methyl-3,4-dihydro-3-oxo-2H-1,4-benzoxazin-2-yl]acetic acid
ethyl 2-[5-fluoro-4-(4,7-difluorobenzothiazol-2-yl)methyl-3,4-dihydro-3-oxo-2H-1,4-benzoxazin-2-yl]acetate
2-[5-fluoro-4-(4,7-difluorobenzothiazol-2-yl)methyl-3,4-dihydro-3-oxo-2H-1,4-benzoxazin-2-yl]acetic acid
ethyl 2-[5-fluoro-4-(5,7-difluorobenzothiazol-2-yl)methyl-3,4-dihydro-3-oxo-2H-1,4-benzoxazin-2-yl]acetate
2-[5-fluoro-4-(5,7-difluorobenzothiazol-2-yl)methyl-3,4-dihydro-3-oxo-2H-1,4-benzoxazin-2-yl]acetic acid
ethyl 2-[5-fluoro-4-(5,6-difluorobenzothiazol-2-yl)methyl-3,4-dihydro-3-oxo-2H-1,4-benzoxazin-2-yl]acetate
2-[5-fluoro-4-(5,6-difluorobenzothiazol-2-yl)methyl-3,4-dihydro-3-oxo-2H-1,4-benzoxazin-2-yl]acetic acid
ethyl 2-[5-fluoro-4-(6,7-difluorobenzothiazol-2-yl)methyl-3,4-dihydro-3-oxo-2H-1,4-benzoxazin-2-yl]acetate
2-[5-fluoro-4-(6,7-difluorobenzothiazol-2-yl)methyl-3,4-dihydro-3-oxo-2H-1,4-benzoxazin-2-yl]acetic acid
ethyl 2-[5-fluoro-4-(4, 5,6-trifluorobenzothiazol-2-yl)methyl-3,4-dihydro-3-oxo-2H-1,4-benzoxazin-2-yl]acetate
2-[5-fluoro-4-(4,5,6-trifluorobenzothiazol-2-yl)methyl-3,4-dihydro-3-oxo-2H-1,4-benzoxazin-2-yl]acetic acid
ethyl 2-[5-fluoro-4-(4, 5,7-trifluorobenzothiazol-2-yl)methyl-3,4-dihydro-3-oxo-2H-1,4-benzoxazin-2-yl]acetate
2-[5-fluoro-4-(4,5,7-trifluorobenzothiazol-2-yl)methyl-3,4-dihydro-3-oxo-2H-1,4-benzoxazin-2-yl]acetic acid
ethyl 2-[5-fluoro-4-(4,6,7-trifluorobenzothiazol-2-yl)methyl-3,4-dihydro-3-oxo-2H-1,4-benzoxazin-2-yl]acetate
2-[5-fluoro-4-(4,6,7-trifluorobenzothiazol-2-yl)methyl-3,4-dihydro-3-oxo-2H-1,4-benzoxazin-2-yl]acetic acid
ethyl 2-[5-fluoro-4-(5,6,7-trifluorobenzothiazol-2-yl)methyl-3,4-dihydro-3-oxo-2H-1,4-benzoxazin-2-yl]acetate
2-[5-fluoro-4-(5,6,7-trifluorobenzothiazol-2-yl)methyl-3,4-dihydro-3-oxo-2H-1,4-benzoxazin-2-yl]acetic acid
2-[4-(4-fluorobenzothiazol-2-yl)methyl-6-methyl-3,4-dihydro-3-oxo-2H-1,4-benzoxazin-2-yl]acetic acid
2-[6-ethyl-4-(5-fluorobenzothiazol-2-yl)methyl-3,4-dihydro-3-oxo-2H-1,4-benzoxazin-2-yl]acetic acid
2-[4-(5-fluorobenzothiazol-2-yl)methyl-6-propyl-3,4-dihydro-3-oxo-2H-1,4-benzoxazin-2-yl]acetic acid
2-[4-(5-fluorobenzothiazol-2-yl)methyl-6-isopropyl-3,4-dihydro-3-oxo-2H-1,4-benzoxazin-2-yl]acetic acid
2-[4-(6-fluorobenzothiazol-2-yl)methyl-6-methyl-3,4-dihydro-3-oxo-2H-1,4-benzoxazin-2-yl]acetic acid
2-[4-(7-fluorobenzothiazol-2-yl)methyl-6-methyl-3,4-dihydro-3-oxo-2H-1,4-benzoxazin-2-yl]acetic acid
2-[4-(4,5-dichlorobenzothiazol-2-yl)methyl-6-methyl-3,4-dihydro-3-oxo-2H-1,4-benzoxazin-2-yl]acetic acid
2-[4-(4,6-dichlorobenzothiazol-2-yl)methyl-6-methyl-3,4-dihydro-3-oxo-2H-1,4-benzoxazin-2-yl]acetic acid
2-[4-(4,7-dichlorobenzothiazol-2-yl)methyl-6-methyl-3,4-dihydro-3-oxo-2H-1,4-benzoxazin-2-yl]acetic acid
2-[4-(5,6-dichlorobenzothiazol-2-yl)methyl-6-methyl-3,4-dihydro-3-oxo-2H-1,4-benzoxazin-2-yl]acetic acid
2-[4-(5,7-dichlorobenzothiazol-2-yl)methyl-6-methyl-3,4-dihydro-3-oxo-2H-1,4-benzoxazin-2-yl]acetic acid
2-[4-(6,7-dichlorobenzothiazol-2-yl)methyl-6-methyl-3,4-dihydro-3-oxo-2H-1,4-benzoxazin-2-yl]acetic acid
2-[4-(4,5,6-trichlorobenzothiazol-2-yl)methyl-6-methyl-3,4-dihydro-3-oxo-2H-1,4-benzoxazin-2-yl]acetic acid
2-[4-(4,5,7-trichlorobenzothiazol-2-yl)methyl-6-methyl-3,4-dihydro-3-oxo-2H-1,4-benzoxazin-2-yl]acetic acid
2-[4-(4,6,7-trichlorobenzothiazol-2-yl)methyl-6-methyl-3,4-dihydro-3-oxo-2H-1,4-benzoxazin-2-yl]acetic acid
2-[4-(5,6,7-trichlorobenzothiazol-2-yl)methyl-6-methyl-3,4-dihydro-3-oxo-2H-1,4-benzoxazin-2-yl]acetic acid
methyl 2-[4-(4,5-difluorobenzothiazol-2-yl)methyl-6-methyl-3,4-dihydro-3-oxo-2H-1,4-benzoxazin-2-yl]acetate
2-[4-(4,5-difluorobenzothiazol-2-yl)methyl-6-methyl-3,4-dihydro-3-oxo-2H-1,4-benzoxazin-2-yl]acetic acid
methyl 2-[4-(4,6-difluorobenzothiazol-2-yl)methyl-6-methyl-3,4-dihydro-3-oxo-2H-1,4-benzoxazin-2-yl]acetate
2-[4-(4,6-difluorobenzothiazol-2-yl)methyl-6-methyl-3,4-dihydro-3-oxo-2H-1,4-benzoxazin-2-yl]acetic acid
methyl 2-[4-(4,7-difluorobenzothiazol-2-yl)methyl-6-methyl-3,4-dihydro-3-oxo-2H-1,4-benzoxazin-2-yl]acetate
2-[4-(4,7-difluorobenzothiazol-2-yl)methyl-6-methyl-3,4-dihydro-3-oxo-2H-1,4-benzoxazin-2-yl]acetic acid
methyl 2-[4-(5,6-difluorobenzothiazol-2-yl)methyl-6-methyl-3,4-dihydro-3-oxo-2H-1,4-benzoxazin-2-yl]acetate
2-[4-(5,6-difluorobenzothiazol-2-yl)methyl-6-methyl-3,4-dihydro-3-oxo-2H-1,4-benzoxazin-2-yl]acetic acid
methyl 2-[4-(5,7-difluorobenzothiazol-2-yl)methyl-6-methyl-3,4-dihydro-3-oxo-2H-1,4-benzoxazin-2-yl]acetate
2-[4-(5,7-difluorobenzothiazol-2-yl)methyl-6-methyl-3,4-dihydro-3-oxo-2H-1,4-benzoxazin-2-yl]acetic acid
methyl 2-[4-(6,7-difluorobenzothiazol-2-yl)methyl-6-methyl-3,4-dihydro-3-oxo-2H-1,4-benzoxazin-2-yl]acetate 2-[4-(6,7-difluorobenzothiazol-2-yl)methyl-6-methyl-3,4-dihydro-3-oxo-2H-1,4-benzoxazin-2-yl]acetic acid
methyl 2-[4-(4,5,6-trifluorobenzothiazol-2-yl)methyl-6-methyl-3,4-dihydro-3-oxo-2H-1,4-benzoxazin-2-yl]acetate
2-[4-(4,5,6-trifluorobenzothiazol-2-yl)methyl-6-methyl-3,4-dihydro-3-oxo-2H-1,4-benzoxazin-2-yl]acetic acid
methyl 2-[4-(4,5,7-trifluorobenzothiazol-2-yl)methyl-6-methyl-3,4-dihydro-3-oxo-2H-1,4-benzoxazin-2-yl]acetate
2-[4-(4,5,7-trifluorobenzothiazol-2-yl)methyl-6-methyl-3,4-dihydro-3-oxo-2H-1,4-benzoxazin-2-yl]acetic acid
methyl 2-[4-(4,6,7-trifluorobenzothiazol-2-yl)methyl-6-methyl-3,4-dihydro-3-oxo-2H-1,4-benzoxazin-2-yl]acetate
2-[4-(4,6,7-trifluorobenzothiazol-2-yl)methyl-6-methyl-3,4-dihydro-3-oxo-2H-1,4-benzoxazin-2-yl]acetic acid
methyl 2-[4-(5,6,7-trifluorobenzothiazol-2-yl)methyl-6-methyl-3,4-dihydro-3-oxo-2H-1,4-benzoxazin-2-yl]acetate
2-[4-(5,6,7-trifluorobenzothiazol-2-yl)methyl-6-methyl-3,4-dihydro-3-oxo-2H-1,4-benzoxazin-2-yl]acetic acid
2-[6-chloro-4-(4-fluorobenzothiazol-2-yl)methyl-3,4-dihydro-3-oxo-2H-1,4-benzoxazin-2-yl]acetic acid
2-[6-chloro-4-(5-fluorobenzothiazol-2-yl)methyl-3,4-dihydro-3-oxo-2H-1,4-benzoxazin-2-yl]acetic acid
2-[6-chloro-4-(6-fluorobenzothiazol-2-yl)methyl-3,4-dihydro-3-oxo-2H-1,4-benzoxazin-2-yl]acetic acid
2-[6-chloro-4-(7-fluorobenzothiazol-2-yl)methyl-3,4-dihydro-3-oxo-2H-1,4-benzoxazin-2-yl]acetic acid
2-[6-chloro-4-(4,5-dichlorobenzothiazol-2-yl)methyl-3,4-dihydro-3-oxo-2H-1,4-benzoxazin-2-yl]acetic acid
2-[6-chloro-4-(4,6-dichlorobenzothiazol-2-yl)methyl-3,4-dihydro-3-oxo-2H-1,4-benzoxazin-2-yl]acetic acid
2-[6-chloro-4-(4,7-dichlorobenzothiazol-2-yl)methyl-3,4-dihydro-3-oxo-2H-1,4-benzoxazin-2-yl]acetic acid
2-[6-chloro-4-(5,6-dichlorobenzothiazol-2-yl)methyl-3,4-dihydro-3-oxo-2H-1,4-benzoxazin-2-yl]acetic acid
2-[6-chloro-4-(5,7-dichlorobenzothiazol-2-yl)methyl-3,4-dihydro-3-oxo-2H-1,4-benzoxazin-2-yl]acetic acid
2-[6-chloro-4-(6,7-dichlorobenzothiazol-2-yl)methyl-3,4-dihydro-3-oxo-2H-1,4-benzoxazin-2-yl]acetic acid
2-[6-chloro-4-(4,5,6-trichlorobenzothiazol-2-yl)methyl-3,4-dihydro-3-oxo-2H-1,4-benzoxazin-2-yl]acetic acid
2-[6-chloro-4-(4,5,7-trichlorobenzothiazol-2-yl)methyl-3,4-dihydro-3-oxo-2H-1,4-benzoxazin-2-yl]acetic acid
2-[6-chloro-4-(4,6,7-trichlorobenzothiazol-2-yl)methyl-3,4-dihydro-3-oxo-2H-1,4-benzoxazin-2-yl]acetic acid
2-[6-chloro-4-(5,6,7-trichlorobenzothiazol-2-yl)methyl-3,4-dihydro-3-oxo-2H-1,4-benzoxazin-2-yl]acetic acid
ethyl 2-[6-chloro-4-(4,5-difluorobenzothiazol-2-yl)methyl-3,4-dihydro-3-oxo-2H-1,4-benzoxazin-2-yl]acetate
2-[6-chloro-4-(4,5-difluorobenzothiazol-2-yl)methyl-3,4-dihydro-3-oxo-2H-1,4-benzoxazin-2-yl]acetic acid
ethyl 2-[6-chloro-4-(4,6-difluorobenzothiazol-2-yl)methyl-3,4-dihydro-3-oxo-2H-1,4-benzoxazin-2-yl]acetate
2-[6-chloro-4-(4,6-difluorobenzothiazol-2-yl)methyl-3,4-dihydro-3-oxo-2H-1,4-benzoxazin-2-yl]acetic acid
ethyl 2-[6-chloro-4-(4,7-difluorobenzothiazol-2-yl)methyl-3,4-dihydro-3-oxo-2H-1,4-benzoxazin-2-yl]acetate
2-[6-chloro-4-(4,7-difluorobenzothiazol-2-yl)methyl-3,4-dihydro-3-oxo-2H-1,4-benzoxazin-2-yl]acetic acid
ethyl 2-[6-chloro-4-(5,6-difluorobenzothiazol-2-yl)methyl-3,4-dihydro-3-oxo-2H-1,4-benzoxazin-2-yl]acetate
2-[6-chloro-4-(5,6-difluorobenzothiazol-2-yl)methyl-3,4-dihydro-3-oxo-2H-1,4-benzoxazin-2-yl]acetic acid
ethyl 2-[6-chloro-4-(5,7-difluorobenzothiazol-2-yl)methyl-3,4-dihydro-3-oxo-2H-1,4-benzoxazin-2-yl]acetate
2-[6-chloro-4-(5,7-difluorobenzothiazol-2-yl)methyl-3,4-dihydro-3-oxo-2H-1,4-benzoxazin-2-yl]acetic acid
ethyl 2-[6-chloro-4-(6,7-difluorobenzothiazol-2-yl)methyl-3,4-dihydro-3-oxo-2H-1,4-benzoxazin-2-yl]acetate
2-[6-chloro-4-(6,7-difluorobenzothiazol-2-yl)methyl-3,4-dihydro-3-oxo-2H-1,4-benzoxazin-2-yl]acetic acid
ethyl 2-[6-chloro-4-(4,5,6-trifluorobenzothiazol-2-yl)methyl-3,4-dihydro-3-oxo-2H-1,4-benzoxazin-2-yl]acetate
2-[6-chloro-4-(4,5,6-trifluorobenzothiazol-2-yl)methyl-3,4-dihydro-3-oxo-2H-1,4-benzoxazin-2-yl]acetic acid
ethyl 2-[6-chloro-4-(4,5,7-trifluorobenzothiazol-2-yl)methyl-3,4-dihydro-3-oxo-2H-1,4-benzoxazin-2-yl]acetate
2-[6-chloro-4-(4,5,7-trifluorobenzothiazol-2-yl)methyl-3,4-dihydro-3-oxo-2H-1,4-benzoxazin-2-yl]acetic acid
ethyl 2-[6-chloro-4-(4,6,7-trifluorobenzothiazol-2-yl)methyl-3,4-dihydro-3-oxo-2H-1,4-benzoxazin-2-yl]acetate
2-[6-chloro-4-(4,6,7-trifluorobenzothiazol-2-yl)methyl-3,4-dihydro-3-oxo-2H-1,4-benzoxazin-2-yl]acetic acid
ethyl 2-[6-chloro-4-(5,6,7-trifluorobenzothiazol-2-yl)methyl-3,4-dihydro-3-oxo-2H-1,4-benzoxazin-2-yl]acetate
2-[6-chloro-4-(5,6,7-trifluorobenzothiazol-2-yl)methyl-3,4-dihydro-3-oxo-2H-1,4-benzoxazin-2-yl]acetic acid
2-[6-fluoro-4-(4-fluorobenzothiazol-2-yl)methyl-3,4-dihydro-3-oxo-2H-1,4-benzoxazin-2-yl]acetic acid
2-[6-fluoro-4-(5-fluorobenzothiazol-2-yl)methyl-3,4-dihydro-3-oxo-2H-1,4-benzoxazin-2-yl]acetic acid
2-[6-fluoro-4-(6-fluorobenzothiazol-2-yl)methyl-3,4-dihydro-3-oxo-2H-1,4-benzoxazin-2-yl]acetic acid
2-[6-fluoro-4-(7-fluorobenzothiazol-2-yl)methyl-3,4-dihydro-3-oxo-2H-1,4-benzoxazin-2-yl]acetic acid
2-[4-(4,5-dichlorobenzothiazol-2-yl)methyl-6-fluoro-3,4-dihydro-3-oxo-2H-1,4-benzoxazin-2-yl]acetic acid
2-[4-(4,6-dichlorobenzothiazol-2-yl)methyl-6-fluoro-3,4-dihydro-3-oxo-2H-1,4-benzoxazin-2-yl]acetic acid
2-[4-(4,7-dichlorobenzothiazol-2-yl)methyl-6-fluoro-3,4-dihydro-3-oxo-2H-1,4-benzoxazin-2-yl]acetic acid
2-[4-(5,6-dichlorobenzothiazol-2-yl)methyl-6-fluoro-3,4-dihydro-3-oxo-2H-1,4-benzoxazin-2-yl]acetic acid
2-[4-(5,7-dichlorobenzothiazol-2-yl)methyl-6-fluoro-3,4-dihydro-3-oxo-2H-1,4-benzoxazin-2-yl]acetic acid
2-[4-(6,7-dichlorobenzothiazol-2-yl)methyl-6-fluoro-3,4-dihydro-3-oxo-2H-1,4-benzoxazin-2-yl]acetic acid
2-[4-(4,5,6-trichlorobenzothiazol-2-yl)methyl-6-fluoro-3,4-dihydro-3-oxo-2H-1,4-benzoxazin-2-yl]acetic acid
2-[4-(4,5,7-trichlorobenzothiazol-2-yl)methyl-6-fluoro-3,4-dihydro-3-oxo-2H-1,4-benzoxazin-2-yl]acetic acid
2-[4-(4,6,7-trichlorobenzothiazol-2-yl)methyl-6-fluoro-3,4-dihydro-3-oxo-2H-1,4-benzoxazin-2-yl]acetic acid
2-[4-(5,6,7-trichlorobenzothiazol-2-yl)methyl-6-fluoro-3,4-dihydro-3-oxo-2H-1,4-benzoxazin-2-yl]acetic acid
ethyl 2-[6-fluoro-4-(4,5-difluorobenzothiazol-2-yl)methyl-3,4-dihydro-3-oxo-2H-1,4-benzoxazin-2-yl]acetate
2-[6-fluoro-4-(4,5-difluorobenzothiazol-2-yl)methyl-3,4-dihydro-3-oxo-2H-1,4-benzoxazin-2-yl]acetic acid
ethyl 2-[6-fluoro-4-(4,6-difluorobenzothiazol-2-yl)methyl-3,4-dihydro-3-oxo-2H-1,4-benzoxazin-2-yl]acetate
2-[6-fluoro-4-(4,6-difluorobenzothiazol-2-yl)methyl-3,4-dihydro-3-oxo-2H-1,4-benzoxazin-2-yl]acetic acid
ethyl 2-[6-fluoro-4-(4,7-difluorobenzothiazol-2-yl)methyl-3,4-dihydro-3-oxo-2H-1,4-benzoxazin-2-yl]acetate
2-[6-fluoro-4-(4,7-difluorobenzothiazol-2-yl)methyl-3,4-dihydro-3-oxo-2H-1,4-benzoxazin-2-yl]acetic acid
ethyl 2-[6-fluoro-4-(5,6-difluorobenzothiazol-2-yl)methyl-3,4-dihydro-3-oxo-2H-1,4-benzoxazin-2-yl]acetate
2-[6-fluoro-4-(5,6-difluorobenzothiazol-2-yl)methyl-3,4-dihydro-3-oxo-2H-1,4-benzoxazin-2-yl]acetic acid
ethyl 2-[6-fluoro-4-(5,7-difluorobenzothiazol-2-yl)methyl-3,4-dihydro-3-oxo-2H-1,4-benzoxazin-2-yl]acetate
2-[6-fluoro-4-(5,7-difluorobenzothiazol-2-yl)methyl-3,4-dihydro-3-oxo-2H-1,4-benzoxazin-2-yl]acetic acid
ethyl 2-[6-fluoro-4-(6,7-difluorobenzothiazol-2-yl)methyl-3,4-dihydro-3-oxo-2H-1,4-benzoxazin-2-yl]acetate 2-[6-fluoro-4-(6,7-difluorobenzothiazol-2-yl)methyl-3,4-dihydro-3-oxo-2H-1,4-benzoxazin-2-yl]acetic acid
ethyl 2-[6-fluoro-4-(4,5,6-trifluorobenzothiazol-2-yl)methyl-3,4dihydro-3-oxo-2H-1,4-benzoxazin-2-yl]acetate
2-[6-fluoro-4-(4,5,6-trifluorobenzothiazol-2-yl)methyl-3,4-dihydro-3-oxo-2H-1,4-benzoxazin-2-yl]acetic acid
ethyl 2-[6-fluoro-4-(4,5,7-trifluorobenzothiazol-2-yl)methyl-3,4-dihydro-3-oxo-2H-1,4-benzoxazin-2-yl]acetate
2-[6-fluoro-4-(4,5,7-trifluorobenzothiazol-2-yl)methyl-3,4-dihydro-3-oxo-2H-1,4-benzoxazin-2-yl]acetic acid
ethyl 2-[6-fluoro-4-(4,6,7-trifluorobenzothiazol-2-yl)methyl-3,4-dihydro-3-oxo-2H-1,4-benzoxazin-2-yl]acetate
2-[6-fluoro-4-(4,6,7-trifluorobenzothiazol-2-yl)methyl-3,4-dihydro-3-oxo-2H-1,4-benzoxazin-2-yl]acetic acid
ethyl 2-[6-fluoro-4-(5,6,7-trifluorobenzothiazol-2-yl)methyl-3,4-dihydro-3-oxo-2H-1,4-benzoxazin-2-yl]acetate
2-[6-fluoro-4-(5,6,7-trifluorobenzothiazol-2-yl)methyl-3,4-dihydro-3-oxo-2H-1,4-benzoxazin-2-yl]acetic acid
2-[4-(4-fluorobenzothiazol-2-yl)methyl-7-methyl-3,4-dihydro-3-oxo-2H-1,4-benzoxazin-2-yl]acetic acid
-[7-ethyl-4-(5-fluorobenzothiazol-2-yl)methyl-3,4-dihydro-3-oxo-2H-1,4-benzoxazin-2-yl]acetic acid
2-[4-(5-fluorobenzothiazol-2-yl)methyl-7-propyl-3,4-dihydro-3-oxo-2H-1,4-benzoxazin-2-yl]acetic acid
2-[4-(5-fluorobenzothiazol-2-yl)methyl-7-isopropyl-3,4-dihydro-3-oxo-2H-1,4-benzoxazin-2-yl]acetic acid
2-[4-(6-fluorobenzothiazol-2-yl)methyl-7-methyl-3,4-dihydro-3-oxo-2H-1,4-benzoxazin-2-yl]acetic acid
2-[4-(7-fluorobenzothiazol-2-yl)methyl-7-methyl-3,4-dihydro-3-oxo-2H-1,4-benzoxazin-2-yl]acetic acid
2-[4-(4,5-dichlorobenzothiazol-2-yl)methyl-7-methyl-3,4-dihydro-3-oxo-2H-1,4-benzoxazin-2-yl]acetic acid
2-[4-(4,6-dichlorobenzothiazol-2-yl)methyl-7-methyl-3,4-dihydro-3-oxo-2H-1,4-benzoxazin-2-yl]acetic acid
2-[4-(4,7-dichlorobenzothiazol-2-yl)methyl-7-methyl-3,4-dihydro-3-oxo-2H-1,4-benzoxazin-2-yl]acetic acid
2-[4-(5,6-dichlorobenzothiazol-2-yl)methyl-7-methyl-3,4-dihydro-3-oxo-2H-1,4-benzoxazin-2-yl]acetic acid
2-[4-(5,7-dichlorobenzothiazol-2-yl)methyl-7-methyl-3,4-dihydro-3-oxo-2H-1,4-benzoxazin-2-yl]acetic acid
2-[4-(6,7-dichlorobenzothiazol-2-yl)methyl-7-methyl-3,4-dihydro-3-oxo-2H-1,4-benzoxazin-2-yl]acetic acid
2-[4-(4,5,6-trichlorobenzothiazol-2-yl)methyl-7-methyl-3,4-dihydro-3-oxo-2H-1,4-benzoxazin-2-yl]acetic acid
2-[4-(4,5,7-trichlorobenzothiazol-2-yl)methyl-7-methyl-3,4-dihydro-3-oxo-2H-1,4-benzoxazin-2-yl]acetic acid
2-[4-(4,6,7-trichlorobenzothiazol-2-yl)methyl-7-methyl-3,4-dihydro-3-oxo-2H-1,4-benzoxazin-2-yl]acetic acid
2-[4-(5,6,7-trichlorobenzothiazol-2-yl)methyl-7-methyl-3,4-dihydro-3-oxo-2H-1,4-benzoxazin-2-yl]acetic acid
ethyl 2-[4-(4,5-difluorobenzothiazol-2-yl)methyl-7-methyl-3,4-dihydro-3-oxo-2H-1,4-benzoxazin-2-yl]acetate
2-[4-(4,5-difluorobenzothiazol-2-yl)methyl-7-methyl-3,4-dihydro-3-oxo-2H-1,4-benzoxazin-2-yl]acetic acid
ethyl 2-[4-(4,6-difluorobenzothiazol-2-yl)methyl-7-methyl-3,4-dihydro-3-oxo-2H-1,4-benzoxazin-2-yl]acetate
2-[4-(4,6-difluorobenzothiazol-2-yl)methyl-7-methyl-3,4-dihydro-3-oxo-2H-1,4-benzoxazin-2-yl]acetic acid
ethyl 2-[4-(4,7-difluorobenzothiazol-2-yl)methyl-7-methyl-3,4-dihydro-3-oxo-2H-1,4-benzoxazin-2-yl]acetate
2-[4-(4,7-difluorobenzothiazol-2-yl)methyl-7-methyl-3,4-dihydro-3-oxo-2H-1,4-benzoxazin-2-yl]acetic acid
ethyl 2-[4-(5,6-difluorobenzothiazol-2-yl)methyl-7-methyl-3,4-dihydro-3-oxo-2H-1,4-benzoxazin-2-yl]acetate
2-[4-(5,6-difluorobenzothiazol-2-yl)methyl-7-methyl-3,4-dihydro-3-oxo-2H-1,4-benzoxazin-2-yl]acetic acid
ethyl 2-[4-(5,7-difluorobenzothiazol-2-yl)methyl-7-methyl-3,4-dihydro-3-oxo-2H-1,4-benzoxazin-2-yl]acetate
2-[4-(5,7-difluorobenzothiazol-2-yl)methyl-7-methyl-3,4-dihydro-3-oxo-2H-1,4-benzoxazin-2-yl]acetic acid
ethyl 2-[4-(6,7-difluorobenzothiazol-2-yl)methyl-7-methyl-3,4-dihydro-3-oxo-2H-1,4-benzoxazin-2-yl]acetate
2-[4-(6,7-difluorobenzothiazol-2-yl)methyl-7-methyl-3,4-dihydro-3-oxo-2H-1,4-benzoxazin-2-yl]acetic acid
ethyl 2-[4-(4,5,6-trifluorobenzothiazol-2-yl)methyl-7-methyl-3,4-dihydro-3-oxo-2H-1,4-benzoxazin-2-yl]acetate
2-[4-(4,5,6-trifluorobenzothiazol-2-yl)methyl-7-methyl-3,4-dihydro-3-oxo-2H-1,4-benzoxazin-2-yl]acetic acid
ethyl 2-[4-(4, 5,7-trifluorobenzothiazol-2-yl)methyl-7-methyl-3,4-dihydro-3-oxo-2H-1,4-benzoxazin-2-yl]acetate
2-[4-(4,5,7-trifluorobenzothiazol-2-yl)methyl-7-methyl-3,4-dihydro-3-oxo-2H-1,4-benzoxazin-2-yl]acetic acid
ethyl 2-[4-(4,6,7-trifluorobenzothiazol-2-yl)methyl-7-methyl-3,4-dihydro-3-oxo-2H-1,4-benzoxazin-2-yl]acetate
2-[4-(4,6,7-trifluorobenzothiazol-2-yl)methyl-7-methyl-3,4-dihydro-3-oxo-2H-1,4-benzoxazin-2-yl]acetic acid
ethyl 2-[4-(5, 6,7-trifluorobenzothiazol-2-yl)methyl-7-methyl-3,4-dihydro-3-oxo-2H-1,4-benzoxazin-2-yl]acetate
2-[4-(5,6,7-trifluorobenzothiazol-2-yl)methyl-7-methyl-3,4-dihydro-3-oxo-2H-1,4-benzoxazin-2-yl]acetic acid
2-[7-fluoro-4-(4-fluorobenzothiazol-2-yl)methyl-3,4-dihydro-3-oxo-2H-1,4-benzoxazin-2-yl]acetic acid
2-[7-fluoro-4-(5-fluorobenzothiazol-2-yl)methyl-3,4-dihydro-3-oxo-2H-1,4-benzoxazin-2-yl]acetic acid
2-[7-fluoro-4-(6-fluorobenzothiazol-2-yl)methyl-3,4-dihydro-3-oxo-2H-1,4-benzoxazin-2-yl]acetic acid
2-[7-fluoro-4-(7-fluorobenzothiazol-2-yl)methyl-3,4-dihydro-3-oxo-2H-1,4-benzoxazin-2-yl]acetic acid
2-[4-(4,5-dichlorobenzothiazol-2-yl)methyl-7-fluoro-3,4-dihydro-3-oxo-2H-1,4-benzoxazin-2-yl]acetic acid
2-[4-(4,6-dichlorobenzothiazol-2-yl)methyl-7-fluoro-3,4-dihydro-3-oxo-2H-1,4-benzoxazin-2-yl]acetic acid
2-[4-(4,7-dichlorobenzothiazol-2-yl)methyl-7-fluoro-3,4-dihydro-3-oxo-2H-1,4-benzoxazin-2-yl]acetic acid
2-[4-(5,6-dichlorobenzothiazol-2-yl)methyl-7-fluoro-3,4-dihydro-3-oxo-2H-1,4-benzoxazin-2-yl]acetic acid
2-[4-(5,7-dichlorobenzothiazol-2-yl)methyl-7-fluoro-3,4-dihydro-3-oxo-2H-1,4-benzoxazin-2-yl]acetic acid
2-[4-(6,7-dichlorobenzothiazol-2-yl)methyl-7-fluoro-3,4-dihydro-3-oxo-2H-1,4-benzoxazin-2-yl]acetic acid
2-[4-(4,5,6-trichlorobenzothiazol-2-yl)methyl-7-fluoro-3,4-dihydro-3-oxo-2H-1,4-benzoxazin-2-yl]acetic acid
2-[4-(4, 5,7-trichlorobenzothiazol-2-yl)methyl-7-fluoro-3,4-dihydro-3-oxo-2H-1,4-benzoxazin-2-yl]acetic acid
2-[4-(4,6,7-trichlorobenzothiazol-2-yl)methyl-7-fluoro-3,4-dihydro-3-oxo-2H-1,4-benzoxazin-2-yl]acetic acid
2-[4-(5,6,7-trichlorobenzothiazol-2-yl)methyl-7-fluoro-3,4-dihydro-3-oxo-2H-1,4-benzoxazin-2-yl]acetic acid
ethyl 2-[7-fluoro-4-(4,5-difluorobenzothiazol-2-yl)methyl-3,4-dihydro-3-oxo-2H-1,4-benzoxazin-2-yl]acetate
2-[7-fluoro-4-(4,5-difluorobenzothiazol-2-yl)methyl-3,4-dihydro-3-oxo-2H-1,4-benzoxazin-2-yl]acetic acid
ethyl 2-[7-fluoro-4-(4,6-difluorobenzothiazol-2-yl)methyl-3,4-dihydro-3-oxo-2H-1,4-benzoxazin-2-yl]acetate
2-[7-fluoro-4-(4,6-difluorobenzothiazol-2-yl)methyl-3,4-dihydro-3-oxo-2H-1,4-benzoxazin-2-yl]acetic acid
ethyl 2-[7-fluoro-4-(4,7-difluorobenzothiazol-2-yl)methyl-3,4-dihydro-3-oxo-2H-1,4-benzoxazin-2-yl]acetate
2-[7-fluoro-4-(4,7-difluorobenzothiazol-2-yl)methyl-3,4-dihydro-3-oxo-2H-1,4-benzoxazin-2-yl]acetic acid
ethyl 2-[7-fluoro-4-(5,6-difluorobenzothiazol-2-yl)methyl-3,4-dihydro-3-oxo-2H-1,4-benzoxazin-2-yl]acetate
2-[7-fluoro-4-(5,6-difluorobenzothiazol-2-yl)methyl-3,4-dihydro-3-oxo-2H-1,4-benzoxazin-2-yl]acetic acid
ethyl 2-[7-fluoro-4-(5,7-difluorobenzothiazol-2-yl)methyl-3,4-dihydro-3-oxo-2H-1,4-benzoxazin-2-yl]acetate 2-[7-fluoro-4-(5,7-difluorobenzothiazol-2-yl)methyl-3,4-dihydro-3-oxo-2H-1,4-benzoxazin-2-yl]acetic acid
ethyl 2-[7-fluoro-4-(6,7-difluorobenzothiazol-2-yl)methyl-3,4-dihydro-3-oxo-2H-1,4-benzoxazin-2-yl]acetate
2-[7-fluoro-4-(6,7-difluorobenzothiazol-2-yl)methyl-3,4-dihydro-3-oxo-2H-1,4-benzoxazin-2-yl]acetic acid
ethyl 2-[7-fluoro-4-(4,5,6-trifluorobenzothiazol-2-yl)methyl-3,4-dihydro-3-oxo-2H-1,4-benzoxazin-2-yl]acetate
2-[7-fluoro-4-(4,5,6-trifluorobenzothiazol-2-yl)methyl-3,4-dihydro-3-oxo-2H-1,4-benzoxazin-2-yl]acetic acid
ethyl 2-[7-fluoro-4-(4,5,7-trifluorobenzothiazol-2-yl)methyl-3,4-dihydro-3-oxo-2H-1,4-benzoxazin-2-yl]acetate
2-[7-fluoro-4-(4,5,7-trifluorobenzothiazol-2-yl)methyl-3,4-dihydro-3-oxo-2H-1,4-benzoxazin-2-yl]acetic acid
ethyl 2-[7-fluoro-4-(4,6,7-trifluorobenzothiazol-2-yl)methyl-3,4-dihydro-3-oxo-2H-1,4-benzoxazin-2-yl]acetate
2-[7-fluoro-4-(4,6,7-trifluorobenzothiazol-2-yl)methyl-3,4-dihydro-3-oxo-2H-1,4-benzoxazin-2-yl]acetic acid
ethyl 2-[7-fluoro-4-(5,6,7-trifluorobenzothiazol-2-yl)methyl-3,4-dihydro-3-oxo-2H-1,4-benzoxazin-2-yl]acetate
2-[7-fluoro-4-(5,6,7-trifluorobenzothiazol-2-yl)methyl-3,4-dihydro-3-oxo-2H-1,4-benzoxazin-2-yl]acetic acid
2-[4-(4-fluorobenzothiazol-2-yl)methyl-8-methyl-3,4-dihydro-3-oxo-2H-1,4-benzoxazin-2-yl]acetic acid
2-[8-ethyl-4-(5-fluorobenzothiazol-2-yl)methyl-3,4-dihydro-3-oxo-2H-1,4-benzoxazin-2-yl]acetic acid
2-[4-(5-fluorobenzothiazol-2-yl)methyl-8-propyl-3,4-dihydro-3-oxo-2H-1,4-benzoxazin-2-yl]acetic acid
2-[4-(5-fluorobenzothiazol-2-yl)methyl-8-isopropyl-3,4-dihydro-3-oxo-2H-1,4-benzoxazin-2-yl]acetic acid
2-[4-(6-fluorobenzothiazol-2-yl)methyl-8-methyl-3,4-dihydro-3-oxo-2H-1,4-benzoxazin-2-yl]acetic acid
2-[4-(7-fluorobenzothiazol-2-yl)methyl-8-methyl-3,4-dihydro-3-oxo-2H-1,4-benzoxazin-2-yl]acetic acid
2-[4-(4,5-dichlorobenzothiazol-2-yl)methyl-8-methyl-3,4-dihydro-3-oxo-2H-1,4-benzoxazin-2-yl]acetic acid
2-[4-(4,6-dichlorobenzothiazol-2-yl)methyl-8-methyl-3,4-dihydro-3-oxo-2H-1,4-benzoxazin-2-yl]acetic acid
2-[4-(4,7-dichlorobenzothiazol-2-yl)methyl-8-methyl-3,4-dihydro-3-oxo-2H-1,4-benzoxazin-2-yl]acetic acid
2-[4-(5,6-dichlorobenzothiazol-2-yl)methyl-8-methyl-3,4-dihydro-3-oxo-2H-1,4-benzoxazin-2-yl]acetic acid
2-[4-(5,7-dichlorobenzothiazol-2-yl)methyl-8-methyl-3,4-dihydro-3-oxo-2H-1,4-benzoxazin-2-yl]acetic acid
2-[4-(6,7-dichlorobenzothiazol-2-yl)methyl-8-methyl-3,4-dihydro-3-oxo-2H-1,4-benzoxazin-2-yl]acetic acid
2-[4-(4,5,6-trichlorobenzothiazol-2-yl)methyl-8-methyl-3,4-dihydro-3-oxo-2H-1,4-benzoxazin-2-yl]acetic acid
2-[4-(4,5,7-trichlorobenzothiazol-2-yl)methyl-8-methyl-3,4-dihydro-3-oxo-2H-1,4-benzoxazin-2-yl]acetic acid
2-[4-(4,6,7-trichlorobenzothiazol-2-yl)methyl-8-methyl-3,4-dihydro-3-oxo-2H-1,4-benzoxazin-2-yl]acetic acid
2-[4-(5,6,7-trichlorobenzothiazol-2-yl)methyl-8-methyl-3,4-dihydro-3-oxo-2H-1,4-benzoxazin-2-yl]acetic acid
ethyl 2-[4-(4,5-difluorobenzothiazol-2-yl)methyl-8-methyl-3,4-dihydro-3-oxo-2H-1,4-benzoxazin-2-yl]acetate
2-[4-(4,5-difluorobenzothiazol-2-yl)methyl-8-methyl-3,4-dihydro-3-oxo-2H-1,4-benzoxazin-2-yl]acetic acid
ethyl 2-[4-(4,6-difluorobenzothiazol-2-yl)methyl-8-methyl-3,4-dihydro-3-oxo-2H-1,4-benzoxazin-2-yl]acetate
2-[4-(4,6-difluorobenzothiazol-2-yl)methyl-8-methyl-3,4-dihydro-3-oxo-2H-1,4-benzoxazin-2-yl]acetic acid
ethyl 2-[4-(4,7-difluorobenzothiazol-2-yl)methyl-8-methyl-3,4-dihydro-3-oxo-2H-1,4-benzoxazin-2-yl]acetate
2-[4-(4,7-difluorobenzothiazol-2-yl)methyl-8-methyl-3,4-dihydro-3-oxo-2H-1,4-benzoxazin-2-yl]acetic acid
ethyl 2-[4-(5,6-difluorobenzothiazol-2-yl)methyl-8-methyl-3,4-dihydro-3-oxo-2H-1,4-benzoxazin-2-yl]acetate
2-[4-(5,6-difluorobenzothiazol-2-yl)methyl-8-methyl-3,4-dihydro-3-oxo-2H-1,4-benzoxazin-2-yl]acetic acid
ethyl 2-[4-(5,7-difluorobenzothiazol-2-yl)methyl-8-methyl-3,4-dihydro-3-oxo-2H-1,4-benzoxazin-2-yl]acetate
2-[4-(5,7-difluorobenzothiazol-2-yl)methyl-8-methyl-3,4-dihydro-3-oxo-2H-1,4-benzoxazin-2-yl]acetic acid
ethyl 2-[4-(6,7-difluorobenzothiazol-2-yl)methyl-8-methyl-3,4-dihydro-3-oxo-2H-1,4-benzoxazin-2-yl]acetate
2-[4-(6,7-difluorobenzothiazol-2-yl)methyl-8-methyl-3,4-dihydro-3-oxo-2H-1,4-benzoxazin-2-yl]acetic acid
ethyl 2-[4-(4,5,6-trifluorobenzothiazol-2-yl)methyl-8-methyl-3,4-dihydro-3-oxo-2H-1,4-benzoxazin-2-yl]acetate
2-[4-(4,5,6-trifluorobenzothiazol-2-yl)methyl-8-methyl-3,4-dihydro-3-oxo-2H-1,4-benzoxazin-2-yl]acetic acid
ethyl 2-[4-(4,5,7-trifluorobenzothiazol-2-yl)methyl-8-methyl-3,4-dihydro-3-oxo-2H-1,4-benzoxazin-2-yl]acetate
2-[4-(4,5,7-trifluorobenzothiazol-2-yl)methyl-8-methyl-3,4-dihydro-3-oxo-2H-1,4-benzoxazin-2-yl]acetic acid
ethyl 2-[4-(4,6,7-trifluorobenzothiazol-2-yl)methyl-8-methyl-3,4-dihydro-3-oxo-2H-1,4-benzoxazin-2-yl]acetate
2-[4-(4,6,7-trifluorobenzothiazol-2-yl)methyl-8-methyl-3,4-dihydro-3-oxo-2H-1,4-benzoxazin-2-yl]acetic acid
ethyl 2-[4-(5,6,7-trifluorobenzothiazol-2-yl)methyl-8-methyl-3,4-dihydro-3-oxo-2H-1,4-benzoxazin-2-yl]acetate
2-[4-(5,6,7-trifluorobenzothiazol-2-yl)methyl-8-methyl-3,4-dihydro-3-oxo-2H-1,4-benzoxazin-2-yl]acetic acid
2-[8-fluoro-4-(4-fluorobenzothiazol-2-yl)methyl-3,4-dihydro-3-oxo-2H-1,4-benzoxazin-2-yl]acetic acid
2-[8-fluoro-4-(5-fluorobenzothiazol-2-yl)methyl-3,4-dihydro-3-oxo-2H-1,4-benzoxazin-2-yl]acetic acid
2-[8-fluoro-4-(6-fluorobenzothiazol-2-yl)methyl-3,4-dihydro-3-oxo-2H-1,4-benzoxazin-2-yl]acetic acid
2-[8-fluoro-4-(7-fluorobenzothiazol-2-yl)methyl-3,4-dihydro-3-oxo-2H-1,4-benzoxazin-2-yl]acetic acid
2-[4-(4,5-dichlorobenzothiazol-2-yl)methyl-8-fluoro-3,4-dihydro-3-oxo-2H-1,4-benzoxazin-2-yl]acetic acid
2-[4-(4,6-dichlorobenzothiazol-2-yl)methyl-8-fluoro-3,4-dihydro-3-oxo-2H-1,4-benzoxazin-2-yl]acetic acid
2-[4-(4,7-dichlorobenzothiazol-2-yl)methyl-8-fluoro-3,4-dihydro-3-oxo-2H-1,4-benzoxazin-2-yl]acetic acid
2-[4-(5,6-dichlorobenzothiazol-2-yl)methyl-8-fluoro-3,4-dihydro-3-oxo-2H-1,4-benzoxazin-2-yl]acetic acid
2-[4-(5,7-dichlorobenzothiazol-2-yl)methyl-8-fluoro-3,4-dihydro-3-oxo-2H-1,4-benzoxazin-2-yl]acetic acid
2-[4-(6,7-dichlorobenzothiazol-2-yl)methyl-8-fluoro-3,4-dihydro-3-oxo-2H-1,4-benzoxazin-2-yl]acetic acid
2-[4-(4,5,6-trichlorobenzothiazol-2-yl)methyl-8-fluoro-3,4-dihydro-3-oxo-2H-1,4-benzoxazin-2-yl]acetic acid
2-[4-(4,5,7-trichlorobenzothiazol-2-yl)methyl-8-fluoro-3,4-dihydro-3-oxo-2H-1,4-benzoxazin-2-yl]acetic acid
2-[4-(4,6,7-trichlorobenzothiazol-2-yl)methyl-8-fluoro3,4-dihydro-3-oxo-2H-1,4-benzoxazin-2-yl]acetic acid
2-[4-(5,6,7-trichlorobenzothiazol-2-yl)methyl-8-fluoro-3,4-dihydro-3-oxo-2H-1,4-benzoxazin-2-yl]acetic acid
ethyl 2-[8-fluoro-4-(4,5-difluorobenzothiazol-2-yl)methyl-3,4-dihydro-3-oxo-2H-1,4-benzoxazin-2-yl]acetate
2-[8-fluoro-4-(4,5-difluorobenzothiazol-2-yl)methyl-3,4-dihydro-3-oxo-2H-1,4-benzoxazin-2-yl]acetic acid
ethyl 2-[8-fluoro-4-(4,6-difluorobenzothiazol-2-yl)methyl-3,4-dihydro-3-oxo-2H-1,4-benzoxazin-2-yl]acetate
2-[8-fluoro-4-(4,6-difluorobenzothiazol-2-yl)methyl-3,4-dihydro-3-oxo-2i2H-1,4-benzoxazin-2-yl]acetic acid
ethyl 2-[8-fluoro-4-(4,7-difluorobenzothiazol-2-yl)methyl-3,4-dihydro-3-oxo-2H-1,4-benzoxazin-2-yl]acetate
2-[8-fluoro-4-(4,7-difluorobenzothiazol-2-yl)methyl-3,4-dihydro-3-oxo-2H-1,4-benzoxazin-2-yl]acetic acid
ethyl 2-[8-fluoro-4-(5,6-difluorobenzothiazol-2-yl)methyl-3,4-dihydro-3-oxo-2H-1,4-benzoxazin-2-yl]acetate 2-[8-fluoro-4-(5,6-difluorobenzothiazol-2-yl)methyl-3,4-dihydro-3-oxo-2H-1,4-benzoxazin-2-yl]acetic acid
ethyl 2-[8-fluoro-4-(5,7-difluorobenzothiazol-2-yl)methyl-3,4-dihydro-3-oxo-2H-1,4-benzoxazin-2-yl]acetate
2-[8-fluoro-4-(5,7-difluorobenzothiazol-2-yl)methyl-3,4-dihydro-3-oxo-2H-1,4-benzoxazin-2-yl]acetic acid
ethyl 2-[8-fluoro-4-(6,7-difluorobenzothiazol-2-yl)methyl-3,4-dihydro-3-oxo-2H-1,4-benzoxazin-2-yl]acetate
2-[8-fluoro-4-(6,7-difluorobenzothiazol-2-yl)methyl-3,4-dihydro-3-oxo-2H-1,4-benzoxazin-2-yl]acetic acid
ethyl 2-[8-fluoro-4-(4,5,6-trifluorobenzothiazol-2-yl)methyl-3,4-dihydro-3-oxo-2H-1,4-benzoxazin-2-yl]acetate
2-[8-fluoro-4-(4,5,6-trifluorobenzothiazol-2-yl)methyl-3,4-dihydro-3-oxo-2H-1,4-benzoxazin-2-yl]acetic acid
ethyl 2-[8-fluoro-4-(4,5,7-trifluorobenzothiazol-2-yl)methyl-3,4-dihydro-3-oxo-2H-1,4-benzoxazin-2-yl]acetate
2-[8-fluoro-4-(4,5,7-trifluorobenzothiazol-2-yl)methyl-3,4-dihydro-3-oxo-2H-1,4-benzoxazin-2-yl]acetic acid
ethyl 2-[8-fluoro-4-(4,6,7-trifluorobenzothiazol-2-yl)methyl-3,4-dihydro-3-oxo-2H-1,4-benzoxazin-2-yl]acetate
2-[8-fluoro-4-(4,6,7-trifluorobenzothiazol-2-yl)methyl-3,4-dihydro-3-oxo-2H-1,4-benzoxazin-2-yl]acetic acid
ethyl 2-[8-fluoro-4-(5,6,7-trifluorobenzothiazol-2-yl)methyl-3,4-dihydro-3-oxo-2H-1,4-benzoxazin-2-yl]acetate
2-[8-fluoro-4-(5,6,7-trifluorobenzothiazol-2-yl)methyl-3,4-dihydro-3-oxo-2H-1,4-benzoxazin-2-yl]acetic acid The methods for producing the compound (I) of the present invention are described in detail in the following.
Production Method (a)
A compound of the formula (II)

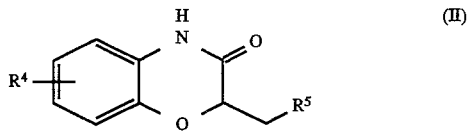

wherein $R^4$ and $R^5$ are as defined above, or a salt thereof, is reacted with a compound of the formula (III)

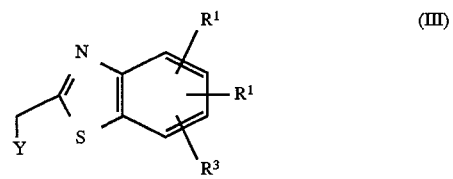

wherein $R_1$, $R^2$ and $R^3$ are as defined above, and Y is halogen atom or $-OSO_2R^6$ wherein $R^6$ is lower alkyl, trifluoromethyl or optionally substituted phenyl, under basic conditions and/or an inert gas atmosphere as necessary, and, where necessary, subjected to hydrolysis to give the compound (I) of the present invention.

Examples of the salt of the compound of the formula (II) are preferably pharmaceutically acceptable salts mentioned above.

The base to be used under the above-mentioned basic conditions is, for example, inorganic base (e.g., alkali metal such as lithium, sodium and potassium; alkaline earth metal such as beryllium, magnesium and calcium; alkali metal hydride such as sodium hydride; alkaline earth metal hydride such as calcium hydride; alkali metal hydroxide such as sodium hydroxide and potassium hydroxide; alkali metal carbonate such as sodium carbonate and potassium carbonate; alkali metal hydrogen-carbonate such as sodium hydrogencarbonate and potassium hydrogencarbonate; alkali metal alkoxide such as sodium methoxide, sodium ethoxide and potassium tert-butoxide; and alkali metal alkanoate such as sodium acetate) and organic base (e.g., trialkylamine such as triethylamine; pyridine compound such as pyridine, lutidine, picoline and 4-dimethylaminopyridine; and quinoline).

The inert gas means nitrogen, argon and the like.

The above-mentioned reactions are generally carried out in various conventional solvents which do not adversely affect the reaction, such as dichloromethane, methanol, ethanol, propanol, pyridine, N,N-dimethylformamide, tetrahydrofuran, dimethyl sulfoxide and a mixture thereof. Preferable solvents include N,N-dimethylformamide, tetrahydrofuran and dimethyl sulfoxide.

While the reaction temperature is not particularly limited, the reaction is generally carried out at a temperature of from under cooling to under heating. For example, when potassium carbonate is used as a base, the reaction temperature is preferably from 0° C. to room temperature.

The hydrolysis is performed by a conventional method in the presence of a base or acid as necessary.

The preferable base includes, for example, alkali metal hydroxides such as sodium hydroxide and potassium hydroxide, and alkali metal carbonates such as sodium carbonate and potassium carbonate. Examples of preferable acid include organic acids such as formic acid, acetic acid, propionic acid, trifluoroacetic acid, benzenesulfonic acid and p-toluenesulfonic acid, and inorganic acids such as hydrochloric acid, hydrobromic acid, sulfuric acid and phosphoric acid.

When the base or acid to be used for said hydrolysis is a liquid, it is generally used as a solvent as well. Alternatively, the hydrolysis can be carried out in a conventional solvent which does not adversely affect the reaction, such as water, acetone, dioxane, dichloromethane, methanol, ethanol, propanol, pyridine, N,N-dimethylformamide and a mixture thereof.

The reaction temperature is not particularly limited and the reaction is generally carried out at a temperature of from under cooling to under heating.

The starting compound of the formula (II) is known or can be easily produced by a known method [Chemical & Pharmaceutical Bulletin, 34(1), 130–139 (1986)].

The starting compound of the formula (III) is known or can be easily produced by a known method [Journal of Medicinal Chemistry, 34, 108–122 (1991)].

Production (b)
A compound of the formula (IV)

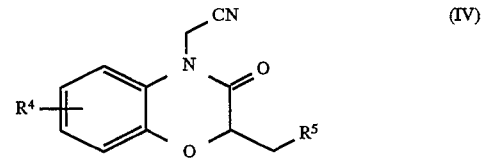

wherein $R^4$ and $R^5$ are as defined above, or a salt thereof, is reacted with a compound of the formula (V)

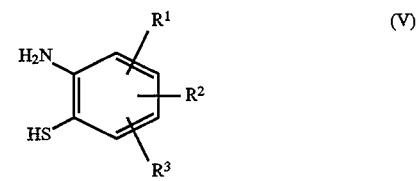

wherein $R^1$, $R^2$ and $R^3$ are as defined above, or an acid addition salt thereof, in the presence of an acid where necessary, which is followed by hydrolysis where necessary, to give the compound (I) of the present invention.

The salts of the compound of the formula (IV) are preferably those pharmaceutically acceptable salts mentioned above.

The preferable solvents in the above-mentioned reactions are, for example, methanol, ethanol and propanol.

Examples of the acid include inorganic acids such as hydrochloric acid, hydrobromic acid, sulfuric acid and nitric acid and organic acids such as formic acid, acetic acid and propionic acid, with preference given to strong acids such as sulfuric acid and hydrochloric acid.

While the reaction temperature is not particularly limited, it is preferably from 60° C. to refluxing temperature.

When the solvent is not used, the compound of the formula (IV) may be reacted with a compound of the formula (V), preferably an acid addition salt thereof (e.g., hydrochloride), by co-melting them at 130–180° C.

The hydrolysis is performed under the same conditions as in the above-mentioned Production (a).

The starting compound of the formula (IV) is obtained by reacting the compound of the formula (II) with a compound of the formula (VI)

(VI)

wherein Z is halogen atom (same as the above-mentioned), under suitable basic conditions and/or an inert gaseous atmosphere.

The base to be used under the above-mentioned basic conditions is, for example, alkali metal hydride such as sodium hydride; alkaline earth metal hydride such as calcium hydride; alkali metal hydroxide such as sodium hydroxide and potassium hydroxide; alkali metal carbonate such as sodium carbonate and potassium carbonate; alkali metal hydrogencarbonate such as sodium hydrogencarbonate and potassium hydrogencarbonate; alkali metal alkoxide such as sodium methoxide, sodium ethoxide and potassium tert-butoxide; and alkali metal alkanoate such as sodium acetate.

The inert gas means nitrogen and argon.

The above-mentioned reactions are generally carried out in various conventional solvents which do not adversely affect the reaction, such as dichloromethane, methanol, ethanol, propanol, pyridine, N,N-dimethylformamide, tetrahydrofuran, dimethyl sulfoxide and a mixture thereof. Preferable solvents include N,N-dimethylformamide, tetrahydrofuran and dimethyl sulfoxide.

While the reaction temperature is not particularly limited, it is preferably from room temperature to 100° C.

The starting compound of the formula (V) is known or can be easily produced by a known method [Journal of Medicinal Chemistry, 34, 108–122 (1991)].

The compound (I) of the present invention obtained by the above production method can be separated and purified by a conventional method such as extraction, precipitation, fractionation chromatography, separation, crystallization and recrystallization.

The compound (I) of the present invention thus produced can be converted to desired pharmaceutically acceptable salts by a conventional method.

The results of the pharmacological tests to show the effectiveness of the compound (I) of the present invention are given in the following. The similar results were also obtained with regard to the compounds of the present invention that are not exemplified here. 1) Aldose reductase inhibitory action
Preparation of Enzyme An aldose reductase enzyme standard product was prepared from swine lens according to the method of S. Hayman et al. [Journal of Biological Chemistry, 240, 877–882 (1965)]. That is, swine lenses freeze-stored at −80° C. were homogenized with distilled water and centrifuged at 10,000 G for 15 minutes. The supernatant was prepared into a 40% ammonium sulfate solution and subjected to centrifugation at 10,000 G for 10 minutes. The supernatant obtained was dialyzed overnight against a 0.05M sodium chloride solution to give a dialyzed solution, which was used as an enzyme standard product.

Activity Determination

Test compound: Compound of the invention and Compound A (3,4-dihydro-2,8-diisopropyl-3-thioxo-2H-1,4-benzoxazine-4-acetic acid described in Japanese Patent Unexamined Publication No. 107970/1988)

The activity of aldose reductase was determined by the above-mentioned method of S. Hayman et al. That is, the above-mentioned enzyme solution (25 μl) and a drug solution (25 μl) dissolved in 1% DMSO at various concentrations were added to a 40 mM phosphate buffer (200 μl, pH 6.2) containing, at final concentrations, 0.4M lithium sulfate, 0.1 mM NADPH (reduced type nicotinamide adenine dinucleotide phosphate) and 3 mM dl-glyceraldehyde as a substrate. The mixture was allowed to react at 25° C. for 2 minutes and the changes in absorbance at 340 nm were determined with COBAS FARA II (manufactured by Roche). The changes in absorbance when 1% DMSO was added instead of the drug solution was taken as 100%, based on which 50% inhibition concentration (IC$_{50}$) was calculated and shown in Table 1. In the Table, IC$_{50}$ (M) shows the concentration of the drug inhibiting the aldose reductase activity by 50%. The test drug number indicates the example number to be mentioned later. IC$_{50}$ (M) means the concentration of the drug at which the aldose reductase activity is inhibited by 50%

TABLE 1

| Test drug | IC$_{50}$ (M) |
| --- | --- |
| Example 25 | 8.6 × 10$^{-9}$ |
| Example 26 | 9.6 × 10$^{-9}$ |
| Example 27 | 9.9 × 10$^{-9}$ |
| Example 34 | 9.9 × 10$^{-9}$ |
| Example 35 | 9.1 × 10$^{-9}$ |
| Example 36 | 9.2 × 10$^{-9}$ |
| Example 39 | 9.9 × 10$^{-9}$ |
| Compound A | 2.1 × 10$^{-8}$ |

(2) Inhibitory action on sorbitol accumulation in tissues of rats with experimental diabetes Test Drugs: Compound of the invention and Compound A (3,4-dihydro-2,8-diisopropyl-3-thioxo-2H-1,4-benzoxazine-4-acetic acid described in Japanese Patent Unexamined Publication No. 107970/1988)

Sprague-Dawley rats (male, 6 weeks old, 5–6 per group) were fasted for 18 hours and injected with streptozotocin (SIGMA, 60 mg/kg) via the tail vein under etherization to prepare rats with diabetes.

The various compounds were orally administered at 4, 8 and 24 hours after the injection of streptozotocin, at 10 mg/kg or 30 mg/kg as a 0.5% carboxymethylcellulose suspension. During the administrations, the rats were raised under free access to feed and water, and the sorbitol content of the tissues (erythrocytes, sciatic nerve, lens) was determined 3 hours after the final administration, according to the enzyme method of H. Y. Bergmeyer et al. [Methods of Enzymatic Analysis, vol. 3, 1323–1330 (1974)] with the use of SDH (sorbitol dehydrogenase) and NAD (β-nicotinamide adenine dinucleotide). The results (sorbitol accumulation)

are expressed in percent (%) relative to the value of a control group administered with 0.5% carboxymethylcellulose solution (solvent) instead of the drug, which was taken as 100%. The results are shown in Table 2.

TABLE 2

| Test drug | Sorbitol erythrocytes | accumulation (%)[1] nerve | lens |
|---|---|---|---|
| Example 28[a] | 16.3** | 56.0** | 89.3 |
| Example 30[a] | 22.2** | 1.0** | 45.2** |
| Example 32[a] | 27.2** | 11.4** | 39.1** |
| Example 36[a] | 17.3** | 23.5** | 60.7* |
| Example 38[a] | 24.6** | 0.0** | 44.1** |
| Example 43[a] | 34.9** | 60.6** | 100.9 |
| Example 44[a] | 25.9** | 4.7** | 52.0** |
| Example 45[a] | 32.4** | 56.8** | 71.8* |
| Compound A[b] | 53.7* | 54.9** | 87.3 |

[1] The control was taken as 100%.
Tukey's Multiple Range Test: *$p < 0.05$ **$p < 0.01$
[a] 10 mg/kg
[b] 30 mg/kg The acute toxicity of the compound of the present invention was confirmed by the following method.

Normal ICR mice (male, 7 weeks old, 5 per group) were fasted for 18 hours and the compound (300 mg/kg) of Example 33 was orally administered as a 0.5% carboxymethylcellulose suspension. To the control group, a 0.5% carboxymethylcellulose solution alone was orally administered, and observation was continued for 14 days thereafter, during which period the mice were allowed to take feed and water freely.

As a result, there was no case of death among the mice administered with the compound of the present invention, and their weights showed transition in the same manner as in the control group.

As mentioned earlier, the compound of the present invention and pharmaceutically acceptable salts thereof have a superior aldose reductase inhibitory action and superior safety. Accordingly, they are effectively used for the prevention and/or treatment of the complications of diabetes, such as faulty union of corneal injury, cataract, neurosis, retinopathy and nephropathy, in particular, for the prevention and/or treatment of cataract and neurosis, in mammals such as human, cow, horse, dog, mouse, rat and so on.

When the compound of the present invention or a pharmaceutically acceptable salt thereof is administered for the prevention and treatment of the above-mentioned diseases, oral or parenteral administration can be employed.

The compound of the present invention or a pharmaceutically acceptable salt thereof is provided in the form of a solid preparation, semi-solid preparation or liquid preparation together with organic or inorganic carrier and/or excipient suitable for external, oral or local administration. The compound of the present invention and salts thereof are prepared into a dosage form such as tablet, pellet, capsule, suppository, liquid, emulsion or suspension along with non-toxic and pharmacologically acceptable auxiliary ingredients. The auxiliary ingredients include those effectively used for the production of solid, semi-solid or liquid preparations, such as water, glucose, lactose, gelatin, mannitol, starch paste, magnesium trisilicate, corn starch, keratin, colloidal silica, potato starch and urea. The auxiliary ingredients include stabilizer, extender, coloring and aromatic agent. So as to retain the activity of the compound of the present invention and salts thereof, a preservative may be also contained. The pharmaceutical preparation should contain the compound of the present invention or a salt thereof in an amount sufficient to produce the desired preventive and therapeutic effects on the progress or symptom of the target diseases.

When the compound of the present invention or a pharmaceutically acceptable salt thereof is administered to human, it is administered, for example, as an injection or eye drop, or orally in an amount effective for inhibiting aldose reductase or an amount sufficient to prevent and/or treat the complications of diabetes. While the dose of the compound of the present invention and a salt thereof varies depending on age, body weight, symptom, preventive/therapeutic effect, administration route, administration period etc., it is generally administered orally at 1–2000 mg/day, preferably at 10–600 mg/day in one to three doses a day.

The present invention is explained in more detail in the following by way of Examples and Preparative Examples, to which the present invention is not limited.

EXAMPLE 1

Ethyl 2-[4-(5-chlorobenzothiazol-2-yl) methyl-3,4-dihydro-3-oxo-2H-1,4-benzoxazin-2-yl]acetate Ethyl 2-(3,4-dihydro-3-oxo-2H-1,4-benzoxazin-2-yl] acetate (150 mg), 2-bromomethyl-5-chlorobenzothiazole (186 mg) and potassium iodide (13 mg) were dissolved in dimethyl sulfoxide (2 ml). Potassium carbonate (133 mg) was added and the mixture was stirred at room temperature for 15 hours. A saturated aqueous solution of ammonium chloride was added to the reaction mixture, and the mixture was extracted with ethyl acetate. The organic layer was washed with saturated brine and dried over anhydrous sodium sulfate, and the solvent was distilled away.

The obtained oily residue was purified by silica gel chromatography to give 146 mg of the title compound. The structural formula and properties of this compound are shown in Table 3.

EXAMPLE 2

Ethyl 2-[6-fluoro-4-(4,5,7-trifluorobenzothiazol-2-yl) methyl-3,4-dihydro-3-oxo-2H-1,4-benzoxazin-2-yl]acetate Ethyl 2-(4-cyanomethyl-6-fluoro-3,4-dihydro-3-oxo-2H-1,4-benzoxazin-2-yl]acetate (500 mg) and 2-amino-3,4,6-trifluorothiophenol hydrochloride (388 mg) were added to anhydrous ethanol (5 ml), and the mixture was refluxed under heating under an argon atmosphere. Fifteen hours later, the solvent was distilled away and water was added to the residue, which was followed by extraction with ethyl acetate. The organic layer was dried over anhydrous magnesium sulfate, and the solvent was. distilled away.

The obtained oily substance was subjected to silica gel column chromatography and eluted with dichloromethane-ethyl acetate to give 520 mg of the title compound. The structural formula and properties of this compound are shown in Table 3.

EXAMPLES 3–23

In substantially the same manner as in Example 2, synthesis was performed to give the compounds shown in Tables 3 to 5. The structural formulas and the properties of the compounds obtained in these Examples are shown in Tables 3–5.

EXAMPLE 24

2-[4-(4,5,7-Trifluorobenzothiazol-2-yl) methyl-3,4-dihydro-3-oxo-2H-4-benzoxazin-2-yl]acetic acid The title compound (520 mg) of Example 2 was dissolved in hydrobromic acid (7 ml) and the mixture was stirred at 140° C. for 4.5 hours. Ice water was added and the precipitated solid was crystallized from ethanol to give 400 mg of the title compound. The structural formula and properties of this compound are shown in Table 6.

EXAMPLES 25–46

In substantially the same manner as in Example 24, synthesis was performed to give the compounds shown in Tables 6 to 8. The structural formulas and the properties of the compounds obtained in these Examples are shown in Tables 6 to 8.

Preparative Example 1

Ethyl 2-(4-cyanomethyl-6-fluoro-3,4-dihydro-3-oxo-2H-1,4-benzoxazin-2-yl)acetate Ethyl 2-(6-fluoro-3,4-dihydro-3-oxo-2H-1,4-benzoxazin-2-yl) acetate (1.60 g), bromoacetonitrile (1.4 g) and potassium iodide (125 mg) were dissolved in dimethyl sulfoxide (6 ml). Potassium carbonate (1.31 g) was added and the mixture was stirred at room temperature for 40 hours. A saturated aqueous solution of ammonium chloride was added to the reaction mixture and the mixture was extracted with ethyl acetate. The organic layer was washed with saturated brine and dried over anhydrous sodium sulfate, and the solvent was distilled away.

The obtained semi-crystal residue was dissolved in benzene, and insoluble matters were filtered. The solvent was distilled away and isopropyl ether/ethanol was added to the residue to allow crystallization, whereby 1.24 g of the title compound was obtained. The structural formula and the properties of this compound are shown in Table 9.

Preparative Examples 2–6

In substantially the same manner as in Preparative Example 1, synthesis was performed to give the compounds shown in Table 9. The structural formulas and the properties of the compounds obtained in these Preparative Examples are shown in Table 9.

In Tables 3 to 8, $R^1$ to $R^3$ denote hydrogen unless otherwise indicated.

TABLE 3

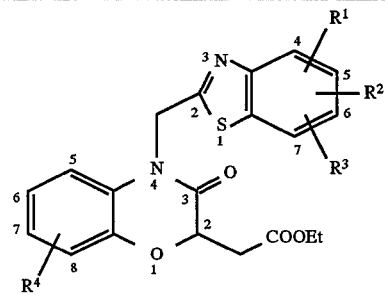

| Ex. No. | $R^1,R^2,R^3$ | $R^4$ | NMR (CDCl$_3$) δ in ppm scale | MS(EI) m/z |
|---|---|---|---|---|
| 1 | 5-Cl | H | 1.30(3H, t), 3.02(1H, dd), 3.19(1H, dd), 4.24(2H, q), 5.08(1H, dd), 5.41(1H, d), 5.61(1H, dd), 6.97–7.20(4H, m), 7.36(1H, dd), 7.74(1H, d), 8.02(1H, d) | 418, 416, 234 |
| 2 | 4, 5, 7-F | 6-F | 1.30(3H, t), 3.03(1H, dd), 3.18(1H, dd), 4.24(2H, g), 5.04(1H, dd), 5.40(1H, d), 5.59(1H, d), 6.69–6.76(1H, m), 6.95–7.11(3H, m) | 454, 252 |
| 3 | 4, 5-F | 6-F | 1.26(3H, t), 3.07(1H, dd), 3.16(1H, dd), 4.19(2H, q), 5.18(1H, dd), 5.67(1H, d), 5.75(1H, d), 6.93–7.00(1H, m), 7.12–7.64 (1H, m) 7.90–7.94(1H, m) | 436, 252 |
| 4 | 5, 7-F | 6-F | 1.27(3H, t), 2.25(3H, s), 2.31(3H, s), 2.63(1H, dd), 3.12(1H, dd), 3.97(1H, dd), 4.20(2H, q), 5.46(1H, d), 5.60(1H, d), 6.78(1H, s), 6.99(1H, s), 7.08–7.74(3H, m) | 436, 252 |
| 5 | 4, 5-Cl | 6-F | 1.30(3H, t), 2.99(1H, dd), 3.18(1H, dd), 4.24(2H, q), 5.03(1H, dd), 5.44(1H, d), 5.59(1H, d), 6.68–6.75(1H, m), 6.94–7.04(2H, m), 7.49(1H, m), 7.66(1H, m) | 470, 468, 252 |
| 6 | 5-F | H | 1.29(3H, t), 3.02(1H, dd), 3.19(1H, dd), 4.23(2H, q), 5.07(1H, dd), 5.40(1H, d), 5.60(1H, d), 6.97–7.02(3H, m), 7.12–7.21(2H, m), 7.67–7.77(2H, m) | 399, 233 |
| 7 | 4, 5, 7-F | H | 1.30(3H, t), 3.04(1H, dd), 3.19(1H, dd), 4.23(2H, q), 5.08(1H, dd), 5.46(1H, d), 5.62(1H, d), 7.02–7.21(5H, m) | 436, 234 |
| 8 | 4, 5-F | H | 1.29(3H, t), 3.02(1H, dd), 3.18(1H dd), 4.23(2H, q), 5.07(1H, dd), 5.46(1H, d), 5.62(1H, d), 6.68–7.56(6H, m) | 418, 373 |
| 9 | 5, 7-F | H | 1.30(3H, t), 3.02(1H, dd), 3.19(1H, dd), | 418, |

TABLE 3-continued

| Ex. No. | R¹,R²,R³ | R⁴ | NMR (CDCl₃) δ in ppm scale | MS(EI) m/z |
|---|---|---|---|---|
| | | | 4.23(2H, q), 5.08(1H, dd), 5.41(1H, d), 5.60(1H, d), 6.89~7.57(6H, m) | 234 |

TABLE 4

| Ex. No. | R¹,R²,R³ | R⁴ | NMR (CDCl₃) δ in ppm scale | MS(EI) m/z |
|---|---|---|---|---|
| 10 | 6, 7-F | H | 1.30(3H, t), 3.03(1H, dd), 3.20(1H, dd), 4.24(2H, q), 5.08(1H, dd), 5.39(1H, d), 5.59(1H, d), 6.98~7.78(6H, m) | 418, 234 |
| 11 | 4, 5-Cl | H | 1.30(3H, t), 3.04(1H, dd), 3.19(1H, dd), 4.24 2H, q), 5.08(1H, dd), 5.51(1H, d), 5.64(1H, d) 6.98~7.02(4H, m), 7.47(1H, d), 7.64(1H, d) | 452, 450, 234 |
| 12 | 4, 5, 7-F | 6-Me | 1.30(3H, t), 2.27(3H, s), 3.01(1H, dd), 3.18(1H, dd), 4.24(2H, q), 5.02(1H, dd), 5.45(1H, d), 5.59(1H, d), 6.81~7.10(4H, m) | 450, 248, |
| 13 | 4, 5-F | 6-Me | 1.30(3H, t), 2.27(3H, s), 3.00(1H, dd), 3.17(1H, dd), 4.24(2H, q), 5.03(1H, dd), 5.45(1H, d), 5.60(1H, d), 6.80~7.53(5H, m) | 432, 248, |
| 14 | 5, 7-F | 6-Me | 1.30(3H, t), 2.27(3H, s), 3.00(1H, dd), 3.18(1H, dd), 4.24(2H, q), 5.03(1H, dd), 5.40(1H, d), 5.58(1H, d), 6.81~7.58(5H, m) | 432, 248 |
| 15 | 4, 5, 7-F | 6-Cl | 1.30(3H, t), 3.04(1H, dd), 3.18(1H, dd), 4.23(2H q), 5.05(1H, dd), 5.42(1H, d), 5.59(1H, d), 6.93~7.20(4H, m) | 470, 425, 268, 202 |
| 16 | 4, 5-F | 6-Cl | 1.29(3H, t), 3.02(1H, dd), 3.17(1H, dd), 4.23(2H, q), 5.04(1H, dd), 5.41(1H, d), 5.58(1H, d), 6.92~7.54(5H, m) | 452, 407, 268, 184 |
| 17 | 5, 7-F | 6-Cl | 1.29(3H, t), 3.02(1H, dd), 3.18(1H, dd), 4.23(2H, q), 5.05(1H, dd), 5.35(1H, d), 5.57(1H, d), 6.92~7.59(5H, m) | 452, 407, 268, 184 |
| 18 | 4, 5, 7-F | 7-Me | 1.30(3H, t), 2.27(3H, s), 3.02(1H, dd), 3.18(1H, dd), 4.24(2H, q), 5.05(1H, dd) 5.46(1H, d), 5.58(1H, d), 6.79~6.84(2H, m) 7.00~7.09(2H, m) | 450, 248 |
| 19 | 4, 5-F | 7-Me | 1.30(3H, t), 2.26(3H, s), 3.01(1H, dd), 3.18(1H, dd), 4.24(2H, q), 5.05(1H, dd), 5.46(1H, d), 5.59(1H, d), 6.78~7.07(3H, m), 7.21~7.52(2H, m) | 432, 248 |

TABLE 5

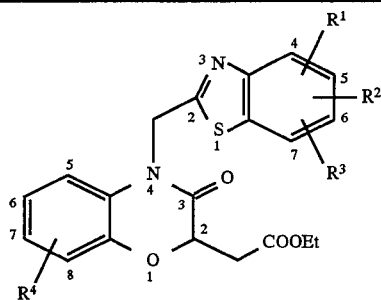

| Ex. No. | $R^1,R^2,R^3$ | $R^4$ | NMR (CDCl$_3$) δ in ppm scale | MS(EI) m/z |
|---|---|---|---|---|
| 20 | 5, 7-F | 7-Me | 1.30(3H, t), 2.27(3H, s), 3.01(1H, dd), 3.18(1H, dd), 4.24(2H, q), 5.06(1H, dd), 5.40(1H, d), 5.57(1H, d), 6.78~7.56(5H, m) | 432, 248, |
| 21 | 4, 5, 7-F | 7-F | 1.30(3H, t), 3.01(1H, dd), 3.18(1H, dd), 4.23(2H q), 5.07(1H, dd), 5.43(1H, d), 5.60(1H, d), 6.70~7.18(4H, m) | 454, 409, 252 |
| 22 | 4, 5-F | 7-F | 1.30(3H, t), 3.03(1H, dd), 3.18(1H, dd), 4.23(2H, q), 5.07(1H, dd), 5.43(1H, d), 5.60(1H, d), 6.69~7.54(5H, m) | 436, 391, 252 |
| 23 | 5, 7-F | 7-F | 1.30(3H, t), 3.03(1H, dd), 3.19(1H, dd), 4.23(2H, q), 5.08(1H, dd), 5.37(1H, d), 5.59(1H, d), 6.69~7.57(5H, m) | 436, 391, 252 |

TABLE 6

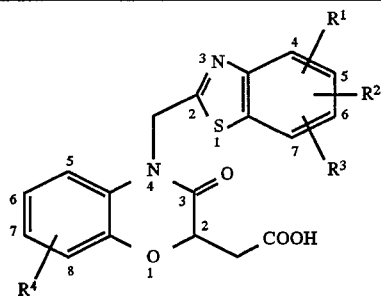

| Ex. No. | $R^1,R^2,R^3$ | $R^4$ | IR(KBr) cm$^{-1}$ | NMR δ in ppm scale [determination solvent] | MS(EI) m/z |
|---|---|---|---|---|---|
| 24 | 4, 5, 7-F | 6-F | 2650~3450, 1732, 1694 | 3.13(1H, dd), 3.27(1H, dd), 5.00(1H, dd), 5.44(1H, d), 5.57(1H, d), 6.70~6.77(1H, m), 6.96~7.10(3H, m) [CDCl$_3$] | 426, 223 |
| 25 | 5-Cl | H | 2500~3500, 1724, 1680 | 3.01(1H, dd), 3.19(1H, dd), 5.08(1H, dd), 5.43(1H, d), 5.61(1H, d), 6.98~7.17(4H, m), 7.38(1H, dd), 7.76(1H, d), 8.01(1H, d) [CDCl$_3$:CD$_3$OD=5:1] | 340, 388, 205 |
| 26 | 4, 5-F | 6-F | 2600~3450, 1732, 1684 | 2.97(1H, dd), 3.17(1H, dd), 5.04(1H, dd), 5.43(1H, d), 5.58(1H, d), 6.70~6.78(1H, m) 6.92~7.02(2H, m), 7.26~7.36(1H, m), 7.54~7.59(1H, m) [CDCl$_3$:CD$_3$OD=5:1] | 408, 223 |
| 27 | 5, 7-F | 6-F | 2650~3450, 1730, 1690 | 2.98(1H, dd), 3.08(1H, dd), 5.14(1H, dd), 5.67(1H, d), 5.74(1H, d), 6.92~7.17(2H, m), 7.30~7.35(1H, m), 7.54~7.62(1H, m), 7.90~7.93(1H, m) [DMSO] | 408, 224, 442, |
| 28 | 4, 5-Cl | 6-F | 2600~3450, 1704, 1676 | 3.01(1H, dd), 3.18(1H, dd), 5.03(1H, dd), 5.47(1H, d), 5.59(1H, d), 6.69~6.76(1H, m) 6.96~7.05(2H, m), 7.50(1H, d), 7.69(1H, d) [CDCl$_3$] | 440, 223 |
| 29 | 5-F | H | 2570~3450, 1714, 1674 | 3.01(1H, dd), 3.19(1H, dd), 5.08(1H, dd), 5.43(1H, d), 5.61(1H, d), 6.98~7.04(3H, m), 7.15~7.22(2H, m), 7.68~7.80(2H, m) [CDCl$_3$:CD$_3$OD=5:1] | 372, 205 |
| 30 | 4, 5, 7-F | H | 2600~ | 3.02(1H, dd), 3.19(1H, dd), 5.08(1H, dd), | 408, |

TABLE 6-continued

[Structure: benzothiazole-CH2-N(aryl)-C(=O)-CH(O-)-CH2-COOH with positions labeled; R1 at 4, R2 at 5, R3 at 6,7 on benzothiazole; aryl ring with positions 5,6,7,8 and R4 at 8]

| Ex. No. | R¹,R²,R³ | R⁴ | IR(KBr) cm⁻¹ | NMR δ in ppm scale [determination solvent] | MS(EI) m/z |
|---|---|---|---|---|---|
|  |  |  | 3072, 1712, 1696 | 5.50(1H, d), 5.63(1H, d), 7.01~7.20(5H, m) [CDCl₃:CD₃OD=5:1] | 206 |
| 31 | 4, 5-F | H | 2500~ 3700, 1715, 1694 | 3.12(1H, dd), 3.28(1H, dd), 5.04(1H, dd), 5.49(1H, d), 5.62(1H, d), 7.00~7.51(6H, m) [CDCl₃] | 390, 206, 184 |
| 32 | 5, 7-F | H | 2600~ 3450, 1710, 1670 | 3.12(1H, dd), 3.28(1H, dd), 5.05(1H, dd), 5.44(1H, d), 5.60(1H, d), 6.88~7.57(6H, m) [CDCl₃] | 390, 206 |

TABLE 7

[Structure: same as above]

| Ex. No. | R¹,R²,R³ | R⁴ | IR(KBr) cm⁻¹ | NMR δ in ppm scale [determination solvent] | MS(EI) m/z |
|---|---|---|---|---|---|
| 33 | 6, 7-F | H | 2550~ 3120, 1732, 1684 | 3.01(1H, dd), 3.18(1H, dd), 5.09(1H, dd), 5.44(1H, d), 5.61(1H, d), 6.99~7.06(3H, m), 7.16~7.21(1H, m), 7.36~7.40(1H, m), 7.75~7.80(1H, m) [CDCl₃:CD₃OD=5:1] | 390, 206 |
| 34 | 4, 5-Cl | H | 2600~ 3450, 1708, 1682 | 3.10(1H, dd), 3.28(1H, dd), 5.05(1H, dd), 5.54(1H, d), 5.62(1H, d), 6.99~7.05(3H, m), 7.17~7.22(1H, m), 7.45(1H, d), 7.60(1H, d) [CDCl₃:CD₃OD=5:1] | 424, 422, 205 |
| 35 | 4, 5, 7-F | 6-Me | 2860~ 3450, 1732 1696 | 2.28(3H, s), 3.00(1H, dd), 3.17(1H, dd), 5.03(1H, dd), 5.48(1H, d), 5.60(1H, d), 6.83~6.97(3H, m), 7.06~7.15(1H, m) [CDCl₃:CD₃OD:5:1] | 422, 220 |
| 36 | 4, 5-F | 6-Me | 2600~ 3400, 1698, 1684 | 2.27(3H, s), 2.99(1H, dd), 3.16(1H, dd), 5.04(1H, dd), 5.48(1H, d), 5.59(1H, d), 6.83~6.99(3H, m), 7.29~7.33(1H, m), 7.53~7.57(1H, m) [CDCl₃:CD₃OD=5:1] | 404, 220 |
| 37 | 5, 7-F | 6-Me | 2570~ 3470, 1730, 1696 | 2.28(3H, s), 2.99(1H, dd), 3.16(1H, dd), 5.04(1H, dd), 5.45(1H, d), 5.60(1H, d), 6.84~7.05(5H, m) [CDCl₃] | 404, 220 |
| 38 | 4, 5, 7-F | 6-Cl | 2500~ 3700, 1710, 1682 | 3.15(1H, dd), 3.25(1H, dd), 5.21(1H, dd), 5.71(1H, d), 5.79(1H, d), 7.14~7.55(4H, m) [CD₃OD] | 442, 239, 202 |
| 39 | 4, 5-F | 6-Cl | 2500~ 3700, 1730, | 3.15(1H, dd), 3.28(1H, dd), 5.23(1H, dd), 5.70(1H, d), 5.79(1H, d), 7.18~7.92(5H, m) [CD₃OD] | 424, 240, 184 |

TABLE 7-continued

| Ex. No. | R¹,R²,R³ | R⁴ | IR(KBr) cm⁻¹ | NMR δ in ppm scale [determination solvent] | MS(EI) m/z |
|---|---|---|---|---|---|
| 40 | 5, 7-F | 6-Cl | 1678 2500~ 3700, 1698, 1676 | 3.11(1H, dd), 3.27(1H, dd), 5.02(1H, dd), 5.38(1H, d), 5.57(1H, d), 6.91~7.59(5H, m) [CDCl$_3$] | 424, 239, 184 |
| 41 | 4, 5, 7-F | 7-Me | 2600~ 3450, 1710, 1692 | 2.27(3H, s), 3.11(1H, dd), 3.27(1H, dd), 5.02(1H, dd), 5.49(1H, d), 5.57(1H, d), 6.79~6.86(2H, m), 6.98~7.07(2H, m) [CDCl$_3$] | 422, 220 |

TABLE 8

| Ex. No. | R¹,R²,R³ | R⁴ | IR(KBr) cm⁻¹ | NMR δ in ppm scale [determination solvent] | MS(EI) m/z |
|---|---|---|---|---|---|
| 42 | 4, 5-F | 7-Me | 2630~ 3470, 1732, 1682 | 2.27(3H, s), 2.99(1H, dd), 3.16(1H, dd), 5.05(1H, dd), 5.48(1H, d), 5.58(1H, d), 6.80~7.06(3H, m), 7.24~7.33(1H, m), 7.50~7.56(1H, m) [CDCl$_3$:CD$_3$OD=5:1] | 404, 220 |
| 43 | 5, 7-F | 7-Me | 2630~ 3480, 1730, 1680 | 2.26(3H, s), 3.10(1H, dd), 3.26(1H, dd), 5.03(1H, dd), 5.43(1H, d), 5.56(1H, d), 6.78~7.03(4H, m), 7.52~7.55(1H, m) [CDCl$_3$] | 404, 220 |
| 44 | 4, 5, 7-F | 7-F | 2400~ 3700, 1716, 1698 | 3.31(1H, dd), 3.28(1H, dd), 5.05(1H, dd), 5.46(1H, d), 5.59(1H, d), 6.71~7.20(4H, m) [CDCl$_3$] | 426, 223, 202 |
| 45 | 4, 5-F | 7-F | 2500~ 3700, 1730, 1692 | 3.12(1H, dd), 3.28(1H, dd), 5.04(1H, dd), 5.45(1H, d), 5.60(1H, d), 6.71~7.54(5H, m) [CDCl$_3$] | 408, 223, 184 |
| 46 | 5, 7-F | 7-F | 2500~ 3700, 1728, 1692 | 3.12(1H, dd), 3.28(1H, dd), 5.05(1H, dd), 5.40(1H, d), 5.58(1H, d), 6.70~7.53(5H, m) [CDCl$_3$] | 408, 223, 184 |

TABLE 9

| Ex. No. | R⁴ | NMR (CDCl₃) δ in ppm scale | MS(EI) m/z |
|---|---|---|---|
| 1 | 6-F | 1.28(3H, t), 2.99(1H, dd), 3.13(1H, dd), 4.21(2H, q), 4.67(1H, d), 4.94(1H, d), 4.96(1H, dd), 6.77~6.83(2H, m), 6.98~7.03(1H, m) | 292, 218 |
| 2 | 6-Me | 1.28(3H, t), 2.37(3H, s), 2.96(1H, dd), 3.11(1H, dd), 4.20(2H, q), 4.69(1H, d), 4.95(1H, d), 4.95(1H, dd), 6.84~6.95 (3H, m) | 288, 214, |
| 3 | H | 1.28(3H, t), 2.99(1H, dd), 3.14(1H, dd), 4.21(2H, q), 4.71(1H, d), 4.97(1H, d), 4.98(1H, dd), 7.04~7.12(4H, m) | 274, 200, |
| 4 | 7-Me | 1.28(3H, t), 2.31(3H, s), 2.96(1H, dd), 3.12(1H, dd), 4.21(2H, q), 4.70(1H, d), 4.93(1H, d), 4.96(1H, dd), 7.08~7.21 (3H, m) | 288, 213 |
| 5 | 6-Cl | 1.28(3H, t), 3.00(1H, dd), 1.31(1H, dd), 4.21(2H, q), 4.67(1H, d), 4.96(1H, d), 4.97(1H, dd) 6.97~7.09(3H, m) | 308, 263 |
| 6 | 6-F | 1.28(3H, t), 2.99(1H, dd), 3.14(1H, dd), 4.21(2H, q), 4.69(1H, d), 4.97(1H, d), 5.00(1H, dd), 6.79~7.02(3H, m) | 292, 247 |

The formulation examples are given in the following.

Formulation Example 1

| | |
|---|---|
| Compound of Example 30 | 20 g |
| Lactose | 315 g |
| Corn starch | 125 g |
| Crystalline cellulose | 25 g |

The above ingredients were homogeneously mixed and an aqueous solution (200 ml) of 7.5% hydroxypropylcellulose was added. The mixture was prepared into granules by an extrusion granulator with the use of a 0.5 mm diameter screen. The granules were immediately rounded and dried. The dry granules were coated with a film coating solution (1.9 kg) Of the following composition by a fluid-type granulator to give enteric-coated granules.

Coating solution:

| | |
|---|---|
| Hydroxypropylmethylcellulose phthalate | 5.0 (w/w)% |
| Stearic acid | 0.25 (w/w)% |
| Methylene chloride | 50.0 (w/w)% |
| Ethanol | 44.75 (w/w)% |

Formulation Example 2

| | |
|---|---|
| Compound of Example 35 | 20 g |
| Lactose | 100 g |
| Corn starch | 36 g |
| Crystalline cellulose | 30 g |
| Calcium carboxymethylcellulose | 10 g |
| Magnesium stearate | 4 g |

The above ingredients were homogeneously mixed and prepared into tablets each weighing 200 mg by a single punch tableting machine with the use of a 7.5 mm diameter punch. Then, the film coating solution of the following composition was spray-coated at 10 mg per tablet to give enteric-coated tablets.

Coating solution:

| | |
|---|---|
| Hydroxypropylmethylcellulose phthalate | 8.0 (w/w)% |
| Glycerol fatty acid ester | 0.4 (w/w)% |
| Methylene chloride | 50.0 (w/w)% |
| White beewax | 0.1 (w/w)% |
| Isopropanol | 41.5 (w/w)% |

Formulation Example 3

| | |
|---|---|
| Compound of Example 41 | 200 g |
| Polysorbate 80 | 20 g |
| PANASETO® 810 | 1780 g |

The above ingredients were mixed and completely dissolved. With the use of a film solution for soft capsules composed of gelatin (100 parts), con. glycerine (30 parts), ethyl p-hydroxybenzoate (0.4 part) and propyl p-hydroxybenzoate (0.2 part), soft capsules containing 200 mg of a drug solution per capsule were prepared by a rotary method.

Formulation Example 4

| | |
|---|---|
| Compound of Example 44 | 100 mg |
| Sodium acetate | 2 mg |
| Acetic acid (for adjusting to pH 5.8) | suitable amount |
| Distilled water | residual amount |
| Total | 10 ml/vial |

An injection having the above formulation was prepared by a conventional method.

Formulation Example 5

| | |
|---|---|
| Compound of Example 46 | 0.05 g |
| Polysorbate 80 | 0.2 g |
| Sodium dihydrogenphosphate 2 hydrate | 0.2 g |
| Disodium hydrogenphosphate 12 hydrate | 0.5 g |
| Sodium chloride | 0.75 g |
| Methyl p-hydroxybenzoate | 0.026 g |
| Propyl p-hydroxybenzoate | 0.014 g |
| Sterile purified water | suitable amount |
| Total | 100 ml |

An eye drop having the above formulation was prepared by a conventional method.

What is claimed is:

1. A 1,4-benzoxazine-2-acetic acid compound of the formula (I)

wherein $R^1$, $R^2$ and $R^3$ may be the same or different and each is a hydrogen atom, a lower alkyl, an alkoxy, a halogen atom or a hydroxy, $R^4$ is a hydrogen atom, a halogen atom, a lower alkyl or an alkoxy, and $R^5$ is an optionally esterified carboxyl, or a pharmaceutically acceptable salt thereof.

2. The 1,4-benzoxazine-2-acetic acid compound of claim 1, wherein $R^5$ in the formula (I) is a carboxyl, or a pharmaceutically acceptable salt thereof.

3. The 1,4-benzoxazine-2-acetic acid compound of claim 1 or claim 2, wherein at least one of $R^1$, $R^2$ and $R^3$ in the formula (I) is a halogen atom, or a pharmaceutically acceptable salt thereof.

4. The 1,4-benzoxazine-2-acetic acid compound of claim 3, wherein the halogen atom is a fluorine atom, or a pharmaceutically acceptable salt thereof.

5. The 1,4-benzoxazine-2-acetic acid compound of claim 1, which is a member selected from the group consisting of 2-[4-(5-chlorobenzothiazol-2-yl) methyl-3,4-dihydro-3-oxo-2H-1,4-benzoxazin-2-yl]acetic acid, 2-[6-fluoro-4-(4,5-difluorobenzothiazol-2-yl) methyl-3,4-dihydro-3-oxo-2H-1,4-benzoxazin-2-yl]acetic acid, 2-[6-fluoro-4-(5,7-difluorobenzothiazol-2-yl) methyl-3,4-dihydro-3-oxo-2H-1,4-benzoxazin-2-yl]acetic acid, 2-[4-(4,5-dichlorobenzothiazol-2-yl) methyl-6-fluoro-3,4-dihydro-3-oxo-2H-1,4-benzoxazin-2-yl]acetic acid, 2-[4-(4,5,7-trifluorobenzothiazol-2-yl) -methyl-3, 4-dihydro-3-oxo-2H-1,4-benzoxazin-2-yl]acetic acid, 2-[4-(5,7-difluorobenzothiazol-2-yl) methyl-3,4-dihydro-3-oxo-2H-1,4-benzoxazin-2-yl ]acetic acid, 2-[4-(4,5-dichlorobenzothiazol-2-yl) methyl-3,4-dihydro-3-oxo-2H-1,4-benzoxazin-2-yl]acetic acid, 2-[4-(4, 5,7-trifluorobenzothiazol-2-yl) methyl-6-methyl-3,4-dihydro-3-oxo-2H-1,4-benzoxazin-2-yl]acetic acid, 2-[4-(4,5-difluorobenzothiazol-2-yl) methyl-6-methyl-3,4-dihydro-3-oxo-2H-1,4-benzoxazin-2-yl]acetic acid, 2-[6-chloro-4-(4,5, 7-trifluoro-benzothiazol-2-yl) methyl-3,4-dihydro-3-oxo-2H-1,4-benzoxazin-2-yl]acetic acid, 2-[6-chloro-4-(4,5-difluorobenzothiazol-2-yl) methyl-3,4-dihydro-3-oxo-2H-1, 4-benzoxazin-2-yl]acetic acid, 2-[4-(5,7-difluorobenzothiazol-2-yl) methyl-7-methyl-3,4-dihydro-3-oxo-2H-1,4-benzoxazin-2-yl]acetic acid, 2-[7-fluoro-4-(4,5,7-trifluorobenzothiazol-2-yl) methyl-3,4-dihydro-3-oxo-2H-1,4-benzoxazin-2-yl]acetic acid and 2-[7-fluoro-4-(4,5-difluorobenzothiazol-2-yl) methyl-3,4-dihydro-3-oxo-2H-1,4-benzoxazin-2-yl]acetic acid, or a pharmaceutically acceptable salt thereof.

6. A method for producing 1,4-benzoxazine-2-acetic acid compound of claim 1 or a pharmaceutically acceptable salt thereof, comprising (a) reacting a compound of the formula (II)

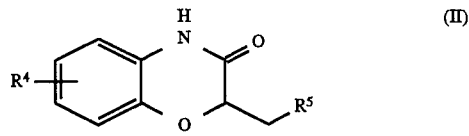

wherein $R^4$ and $R^5$ are as defined above, or a salt thereof, with a compound of the formula (III)

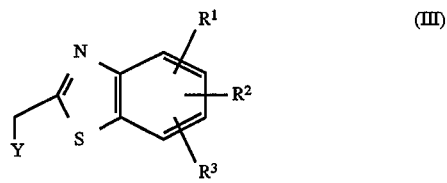

wherein $R^1$, $R^2$ and $R^3$ are as defined above, and Y is a halogen atom or —$OSO_2R^6$ wherein $R^6$ is lower alkyl, trifluoromethyl or optionally substituted phenyl, or (b) reacting a compound of the formula (IV)

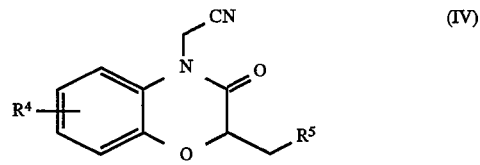

wherein $R^4$ and $R^5$ are as defined above, or a salt thereof, with a compound of the formula (V)

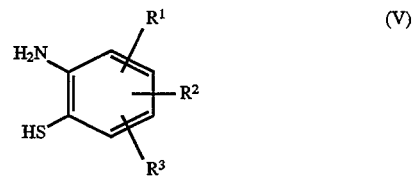

wherein $R^1$, $R^2$ and $R^3$ are as defined above, or an acid addition salt thereof, followed by, on demand, hydrolysis of the compound obtained in the above (a) or (b).

7. A pharmaceutical composition comprising the 1,4-benzoxazine-2-acetic acid compound of claim 1 or a pharmaceutically acceptable salt thereof and a pharmaceutically acceptable carrier.

8. The pharmaceutical composition of claim 7, which is an aldose reductase inhibitor.

9. The pharmaceutical composition of claim 7, which is an agent for the prevention or treatment of the complications of diabetes.

10. A method for inhibiting aldose reductase, comprising administering the 1,4-benzoxazine-2-acetic acid compound of claim 1 or a pharmaceutically acceptable salt thereof in an amount effective for inhibiting aldose reductase.

11. A method for preventing or treating the complications of diabetes, comprising administering the 1,4-benzoxazine-2-acetic acid compound of claim 1 or a pharmaceutically acceptable salt thereof in an amount effective for the prevention or treatment of the complications of diabetes.

* * * * *